US012006357B2

(12) United States Patent
Fassler et al.

(10) Patent No.: US 12,006,357 B2
(45) Date of Patent: Jun. 11, 2024

(54) TRANSTHYRETIN ANTIBODIES AND USES THEREOF

(71) Applicant: Mor Research Applications Ltd., Ramat Gan (IL)

(72) Inventors: Michael Fassler, Ness Ziona (IL); Jacob George, Tel Aviv (IL)

(73) Assignee: MOR RESEARCH APPLICATIONS LTD., Ramat Gan (IL)

( * ) Notice: Subject to any disclaimer, the term of this patent is extended or adjusted under 35 U.S.C. 154(b) by 835 days.

(21) Appl. No.: 17/255,796

(22) PCT Filed: Jun. 26, 2019

(86) PCT No.: PCT/IB2019/055416
§ 371 (c)(1),
(2) Date: Dec. 23, 2020

(87) PCT Pub. No.: WO2020/003172
PCT Pub. Date: Jan. 2, 2020

(65) Prior Publication Data
US 2021/0230257 A1 Jul. 29, 2021

Related U.S. Application Data

(60) Provisional application No. 62/690,116, filed on Jun. 26, 2018.

(51) Int. Cl.
*C07K 16/18* (2006.01)
*A61K 49/00* (2006.01)
*A61P 9/00* (2006.01)
*G01N 33/68* (2006.01)

(52) U.S. Cl.
CPC .......... *C07K 16/18* (2013.01); *A61K 49/0008* (2013.01); *A61P 9/00* (2018.01); *G01N 33/6893* (2013.01); *C07K 2317/14* (2013.01); *C07K 2317/76* (2013.01)

(58) Field of Classification Search
CPC ................ C07K 16/18; C07K 2317/14; C07K 2317/76; A61P 9/00; A61K 49/0008; G01N 33/6893
See application file for complete search history.

(56) References Cited

FOREIGN PATENT DOCUMENTS

| EP | 3101132 A1 | 7/2016 |
|----|---|---|
| WO | WO-2010030203 A1 | 3/2010 |
| WO | WO-2015092077 A1 | 6/2015 |
| WO | WO-2016120811 A1 | 8/2016 |
| WO | WO-2020003172 A1 | 1/2020 |

OTHER PUBLICATIONS

Hosoi, A., et al., "Novel Antibody for the Treatment of Transthyretin Amyloidosis," *The Journal of Biological Chemistry* 291(48):25096-25105, Elsevier Inc., United States (Nov. 2016).

(Continued)

*Primary Examiner* — Aurora M Fontainhas
*Assistant Examiner* — Selam Berhane
(74) *Attorney, Agent, or Firm* — Sterne, Kessler, Goldstein & Fox P.L.L.C.

(57) ABSTRACT

The present disclosure provides antibodies and antigen-binding fragments thereof that specifically bind to human transthyretin (TTR). The anti-TTR antibodies or antigen-binding fragments thereof are useful, for example, in detecting TTR and in treating TTR amyloidosis in a subject.

16 Claims, 22 Drawing Sheets
Specification includes a Sequence Listing.

(56) References Cited

OTHER PUBLICATIONS

International Search Report and Written Opinion for International Application No. PCT/IB2019/055416, Israel Patent Office, Israel, dated Nov. 13, 2019, 9 pages.
Pagourelias, E. D., "Echo Parameters for Differential Diagnosis in Cardiac Amyloidosis: A Head-to-Head Comparison of Deformation and Nondeformation Parameters," *Circulation. Cardiovascular Imaging* 10(3):e005588, Lippincott Williams & Wilkins, United States (Mar. 2017), 11 pages.
Popovic, Z. B., et al., "Speckle-tracking echocardiography correctly identifies segmental left ventricular dysfunction induced by scarring in a rat model of myocardial infarction," *American Journal of Physiology. Heart and Circulatory Physiology* 292(6):H2809-H2816, American Physiological Society, United States (Jun. 2007).
Higaki, J., et al., "Novel conformation-specific monoclonal antibodies against amyloidogenic forms of transthyretin," Amyloid 23(2):86-97, Informa, United Kingdom (Jun. 2016).
George, J., et al., "A novel monoclonal antibody targeting aggregated transthyretin facilitates its removal and functional recovery in an experimental model," *European Heart Journal* 41:1260-1270, Oxford University Press, United Kingdom (2020).

| Transthyretin (state) | ka (1/Ms) | kd (1/s) | KD (M) | KD (nM) |
|---|---|---|---|---|
| Monomer | 2.137E+6 | 0.002295 | 1.074E-9 | 1.074 |
| Fibrillar | 1.926E+6 | 0.001889 | 9.810E-10 | 0.98 |

FIG. 3

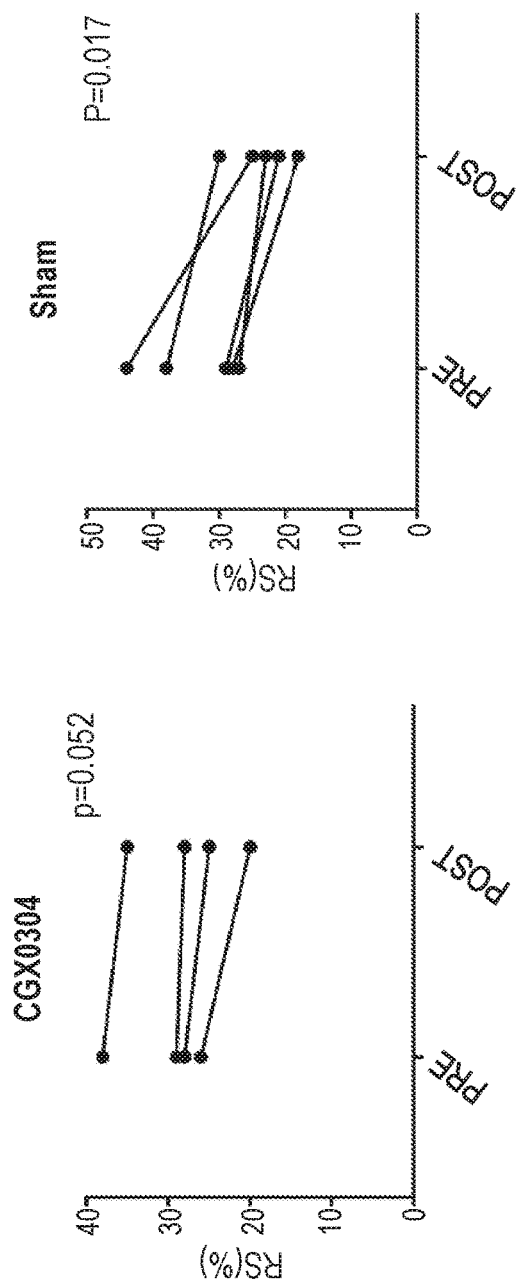
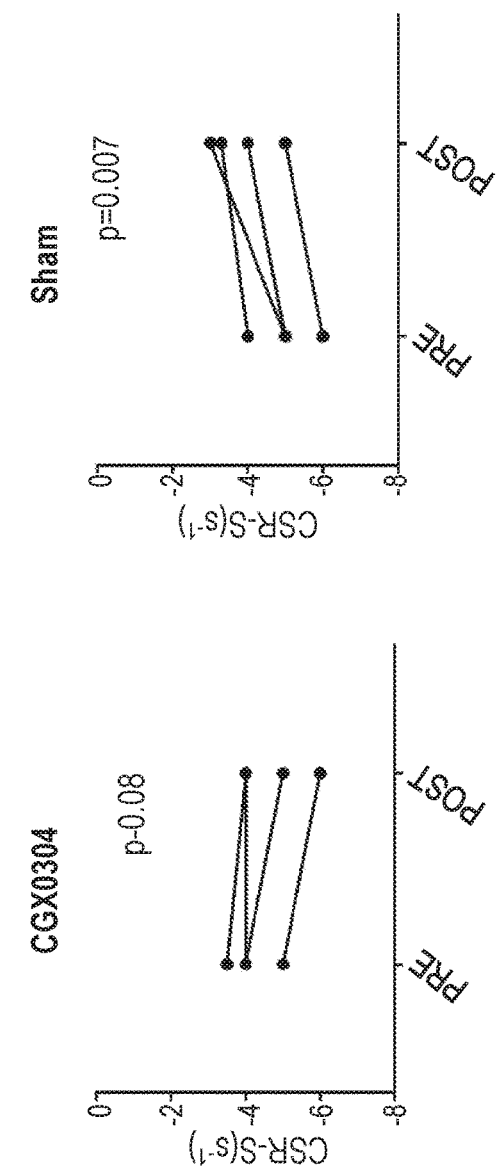
FIG. 14A
FIG. 14B

TRANSTHYRETIN ANTIBODIES AND USES THEREOF

CROSS-REFERENCE TO RELATED APPLICATIONS

This application is a U.S. National Phase of International Application No. PCT/M2019/055416, filed Jun. 26, 2019, which claims priority to U.S. Provisional Application No. 62/690,116, filed Jun. 26, 2018, each of which is herein incorporated by reference in its entirety.

BACKGROUND OF THE INVENTION

Field of the Invention

The present disclosure provides antibodies and antigen-binding fragments thereof that bind to transthyretin (TTR) and methods of using the same.

Background

Transthyretin (TTR), also termed prealbumin, is a soluble, β-sheet rich, 127-amino acid, non-glycosylated protein primarily synthesized and secreted into the blood by the liver. TTR circulates in the blood predominantly as a 55 kDa tetramer, with a minor concentration of dissociated monomer.

The monomeric subunits of TTR fold into a β-sandwich tertiary structure that spontaneously assembles into a tetramer within the cellular endoplasmic reticulum. The tetramer exhibits two distinct dimer-dimer interfaces, the less stable of which makes up two highly conserved thyroxine (T4) binding sites. The three-dimensional structures of the TTR tetramer bound to T4 and its other known ligand, the vitamin A-retinol-binding protein complex, have been solved.

Serum levels of TTR appear to mirror total body nitrogen and total body potassium levels such that they have been suggested to be a marker of nutrition and inflammation, apparently serving as a negative acute phase reactant. The half-life of TTR in blood in vivo is twenty-four to forty-eight hours.

In blood, the TTR tetramer binds retinol-binding protein bound to retinol (holo-retinol-binding protein) and a small amount of T4, and transports them to tissues on the minute-to-hour timescale. Albumin has the highest plasma concentration carrying capacity for T4, and thyroid binding globulin has the highest affinity for T4. Thus, TTR apparently plays a minor role in the physiological transport of T4.

TTR-Triggered Amyloidogenesis

In vitro studies suggest that tetrameric TTR does not form amyloid fibrils and that amyloidogenesis follows tetramer dissociation into dimers, which then rapidly dissociate to folded monomers. Amyloid fibrillogenesis results from exposure of stretches of hydrophobic residues in TTR monomers that subsequently misassemble into spherical aggregates, which then undergo conformational conversion into cross-0 sheet assemblies. Tetramer dissociation is thought to be rate limiting for TTR amyloid formation in the case of the wild-type (WT) protein, and most tetramers produced by heterozygotes contain both mutant and WT TTR subunits.

Clinical Overview of TTR Amyloidosis

The hereditary TTR amyloidosis are rare, autosomal dominant diseases caused by point mutations in the TTR gene. More than one hundred destabilizing mutations of TTR have been identified.

Although the main pathologic manifestation of hereditary TTR amyloidosis is a progressive ascending polyneuropathy and/or cardiomyopathy, mixed phenotypes, extreme variability in the clinical presentation, and incomplete penetrance often result in misdiagnosis by physicians not considering TTR amyloidosis.

Most known cases of TTR-Familial Amyloidotic Polyneuropathy (FAP) result from the Val30Met (p. Val50Met) mutation, frequent in regions of Portugal, Japan, Sweden, and Brazil. TTR-FAP is characterized by a sensory, motor, and autonomic neuropathy. Gastrointestinal symptoms are a common complication of autonomic neuropathy. Amyloid deposits, typically found in ganglia, the endoneurium, and nerve blood vessel gradually lead to destruction of unmyelinated nerve fibers, and then small and large myelinated nerve fibers. Distal axonal degeneration is the main pathogenic feature. Potential underlying mechanisms include: (i) direct toxicity and mechanical stress imposed by modified TTR deposits on nerve fibers; and/or (ii) toxicity of non-amyloid TTR.

Clinical manifestations of cardiac involvement may follow later in the course of disease, but, silent cardiovascular features suggesting heart involvement are not uncommon. Neurologic and cardiac deterioration progress gradually during amyloidogenesis, typically leading to death within five to fifteen years of symptom onset.

In the predominant cardiac phenotype, namely, TTR amyloid cardiomyopathy, amyloid infiltrates unselectively, the valves, ventricles, atria, and the conduction system, leading to left ventricular wall thickening with a non-dilated left ventricle and impaired longitudinal contraction, and results in congestive heart failure and arrhythmias. Mean survival, although not adequately documented is in the range of two years from diagnosis, with death primarily from heart failure or sudden death.

The most prevalent mutation associated with TTR-Familial Amyloidotic Cardiomyopathy (FAC) is Val122Ile (p. Val142Ile), which is found in up to 4% of African Americans. Other pathogenic TTR mutations are less common resulting in a "mixed" phenotype of neurologic and multi-organ system involvement.

In wild-type (WT) TTR amyloidosis, WT TTR tetramers dissociate into monomers, misfold, and undergo amyloidogenesis. Post mortem studies suggest TTR wt phenotype in up to 22-25% of individuals over 80 years of age, and 32% of adults over the age of 75 with heart failure and a preserved ejection fraction. WT TTR amyloidosis is usually a late-onset, sporadic condition primarily affecting men. The prevalence of nervous system involvement among patients with symptomatic WT TTR amyloidosis is approximately 28%, and nearly half have a prior carpal tunnel syndrome apparently owing to amyloid deposition in the connective tissue of the transverse carpal ligament.

Treatment

The only approved treatment for familial TTR amyloidosis is orthotopic liver transplantation. However, WT TTR patients are generally older and unable to tolerate organ transplantation. Additionally, cardiac and peripheral nerve deposition of amyloid continue to progress, despite liver transplant.

Several TTR-stabilizing agents have been developed and are in various stages of clinical trials. Diflunisal, a non-steroidal anti-inflammatory drug (NSAID), binds and stabilizes common familial TTR variants against acid-mediated fibril formation in vitro and has been tested in human clinical trials. Use of diflunisal in transthyretin cardiac amyloidosis (ATTR-CA) is controversial given known consequences of chronic inhibition of cyclooxygenase (COX) enzymes, including gastrointestinal bleeding (COX-1), renal dysfunction (COX-2), fluid retention, and hypertension that may precipitate heart failure (COX-2) in vulnerable individuals.

Tafamidismeglumine ("tafamidis") is a benzoxazole lacking NSAID activity, which makes it ideal for heart failure patients for whom the fluid retention and renal dysfunction caused by NSAIDs may worsen disease manifestations. Tafamid is kinetically stabilizes TTR and inhibits amyloidogenesis. In a double-blind, placebo-controlled, randomized trial of patients with FAP, tafamidis appeared to reduce peripheral neurologic impairment, though the co-primary endpoints, based on the intention to treat two different neuropathy symptom-scoring systems, were not significantly different between treatment and placebo arms. Tafamidis has been approved in Europe and other locations for early stage FAP, but it is still under review in the United States. More clinical trials are underway to evaluate its efficacy in TTR cardiac amyloid patients. Degradation of TTR mRNAs either by short interfering RNA (siRNA) or antisense oligonucleotides has been shown to be an effective method in lowering TTR serum level and halting the progression of amyloid formation. Ionis Pharmaceuticals and Alnylam Pharmaceuticals have both recently reported successful results of antisense oligonucleotides and siRNA, respectively, in FAP. Submissions to the FDA are ongoing.

Given the poor prognosis for patients with TTR amyloidosis, superior detection and treatment reagents are necessary.

BRIEF SUMMARY OF THE INVENTION

Provided herein are antibodies and antigen-binding fragments thereof capable of binding human transthyretin (TTR) and methods of using the same.

In one aspect, an antibody or antigen-binding fragment thereof capable of binding TTR, comprises a complementary determining region (CDR) H1 comprising the amino acid sequence set forth in SEQ ID NO:1 (GYTFTSYY), a CDR H2 comprising the amino acid sequence set forth in SEQ ID NO:2 (IYPGNVNT), a CDR H3 comprising the amino acid sequence set forth in SEQ ID NO:3 (ARTYFDY), a CDR L1 comprising the amino acid sequence set forth in SEQ ID NO:4 (SSVSY), a CDR L2 comprising the amino acid sequence set forth in SEQ ID NO:5 (DTS), and a CDR L3 comprising the amino acid sequence set forth in SEQ ID NO:6 (QQWSSKSFT).

In one aspect, an antibody or antigen-binding fragment thereof capable of binding TTR, comprises a complementary determining region (CDR) H1 comprising the amino acid sequence set forth in SEQ ID NO:8 (SYYIH), a CDR H2 comprising the amino acid sequence set forth in SEQ ID NO:9 (WIYPGNVNTKYNEKFKG), a CDR H3 comprising the amino acid sequence set forth in SEQ ID NO:10 (TYFDY), a CDR L1 comprising the amino acid sequence set forth in SEQ ID NO:11 (SASSSVSYMH), a CDR L2 comprising the amino acid sequence set forth in SEQ ID NO:12 (DTSKLAS), and a CDR L3 comprising the amino acid sequence set forth in SEQ ID NO:6 (QQWSSKSFT).

In one aspect, the antibody or antigen-binding fragment comprises a heavy chain variable region (VH) and a light chain variable region (VL), wherein the VH comprises the same amino acid sequence as the VH of the antibody produced by the hybridoma cell line deposited at the ATCC® as deposit number PTA-125005 on Mar. 14, 2018.

In one aspect, the antibody or antigen-binding fragment comprises a heavy chain variable region (VH) and a light chain variable region (VL), wherein the VL comprises the same amino acid sequence as the VL of the antibody produced by the hybridoma of ATCC® deposit number PTA-125005.

In one aspect, an antibody or antigen-binding fragment thereof that specifically binds to human TTR comprises a VH and a VL, wherein the VH comprises the same amino acid sequence as the VH of the antibody produced by the hybridoma of ATCC® deposit number PTA-125005.

In one aspect, an antibody or antigen-binding fragment thereof that specifically binds to human TTR comprises a VH and a VL, wherein the VL comprises the same amino acid sequence as the VL of the antibody produced by the hybridoma of ATCC® deposit number PTA-125005.

In one aspect, an antibody or antigen-binding fragment thereof capable of binding human TTR comprises a VH comprising the same amino acid sequence as the VH of the antibody produced by the hybridoma of ATCC® deposit number PTA-125005 and a VL comprising the same amino acid sequence as the VL of the antibody produced by the hybridoma of ATCC® deposit number PTA-125005.

In one aspect, the antibody or antigen-binding fragment further comprises a heavy chain constant region. In one aspect, the heavy chain constant region is a human IgG$_1$ heavy chain constant region.

In one aspect, the antibody or antigen-binding fragment further comprises a light chain constant region. In one aspect, the light chain constant region is a human IgGK light chain constant region In one aspect, the antibody or antigen-binding fragment thereof comprises a heavy chain comprising the same amino acid sequence as the heavy chain of the antibody produced by the hybridoma of ATCC® deposit number PTA-125005.

In one aspect, the antibody or antigen-binding fragment thereof comprises a light chain comprising the same amino acid sequence as the light chain of the antibody produced by the hybridoma of ATCC® deposit number PTA-125005.

In one aspect, the antibody or antigen-binding fragment comprises a heavy chain and a light chain comprising the same amino acid sequence as the heavy chain of the antibody produced by the hybridoma of ATCC® deposit number PTA-125005 and the same amino acid sequence as the light chain of the antibody produced by the hybridoma of ATCC® deposit number PTA-125005, respectively.

In one aspect, an antibody or antigen-binding fragment thereof that specifically binds to human TTR comprises the CDR H1, CDR H2, CDR H3, CDR L1, CDR L2, and CDR L3 of the antibody produced by the hybridoma of ATCC® deposit number PTA-125005.

In one aspect, the CDRs are the Kabat-defined CDRs, the Chothia-defined CDRs, or the AbM-defined CDRs.

In one aspect, the antibody or antigen-binding fragment thereof binds to human TTR monomers. In one aspect, the antibody or antigen-binding fragment thereof binds to human TTR fibrils.

In one aspect, the antibody or antigen-binding fragment thereof is capable of decreasing the toxicity of TTR fibrils on human cardiomyocytes. In one aspect, the antibody or antigen-binding fragment thereof is capable of inhibiting the accumulation of TTR aggregates in an organ. In one aspect, the organ is the heart and/or kidney.

Also provided herein are isolated antibodies or antigen-binding fragments thereof that bind to the same epitope of human TTR as any antibody or antigen-binding fragment thereof provided herein.

Also provided herein are isolated antibodies or antigen-binding fragments thereof that competitively inhibit the binding of any antibody or antigen-binding fragment thereof provided herein to human TTR.

In one aspect, the antibody or antigen-binding fragment thereof is a human antibody or antigen-binding fragment thereof. In one aspect, the antibody or antigen-binding fragment thereof is a full-length antibody. In one aspect, the antibody or antigen-binding fragment thereof is an antigen-binding fragment. In one aspect, the antigen-binding fragment comprises a Fab, Fab', F(ab')$_2$, single chain Fv(scFv), disulfide linked Fv, V-NAR domain, IgNar, intrabody, IgGΔCH2, minibody, F(ab')$_3$, tetrabody, triabody, diabody, single domain antibody, DVD-Ig, Fcab, mAb$^2$, (scFv)$_2$, or scFv-Fc.

In one aspect, the antibody or antigen-binding fragment thereof is isolated.

In one aspect, the antibody or antigen-binding fragment further comprises a detectable label.

Also provided herein are isolated polynucleotides comprising a nucleic acid molecule encoding the heavy chain variable region or heavy chain of any antibody or antigen-binding fragment provided herein. In one aspect, the nucleic acid molecule encodes a VH comprising the same amino acid sequence as the VH of the antibody produced by the hybridoma of ATCC® deposit number PTA-125005. In one aspect, the nucleic acid molecule comprises (i) the VH-encoding sequence in the hybridoma of ATCC® deposit number PTA-125005 or (ii) the heavy chain-encoding sequence in the hybridoma of ATCC® deposit number PTA-125005.

Also provided herein are isolated polynucleotides comprising a nucleic acid molecule encoding the light chain variable region or light chain of any antibody or antigen-binding fragment provided herein. In one aspect, the nucleic acid molecule encodes a VL comprising the same amino acid sequence as the VL of the antibody produced by the hybridoma of ATCC® as deposit number PTA-125005. In one aspect, the nucleic acid molecule comprises (i) the VL-encoding sequence in the hybridoma of ATCC® deposit number PTA-125005, (ii) the light chain-encoding sequence in the hybridoma of ATCC® deposit number PTA-125005.

Also provided herein are isolated polynucleotides comprising a nucleic acid molecule encoding the heavy chain variable region or heavy chain of any antibody or antigen-binding fragment thereof provided herein and the light chain variable region or light chain of any antibody or antigen-binding fragment thereof provided herein.

Also provided herein are isolated vectors comprising any polynucleotide provided herein.

Also provided herein are host cells comprising any polynucleotide provided herein, any vector provided herein, or any combination of vectors comprising polynucleotides provided herein. In one aspect, the host cell is selected from the group consisting of CHO, HEK-293T, HeLa and BHK cells, optionally wherein the CHO cell is a CHO-K1SP cell.

Also provided herein are methods of producing an antibody or antigen-binding fragment thereof that binds to human TTR comprising culturing any host cell provided herein so that the nucleic acid molecule is expressed and the antibody or antigen-binding fragment thereof is produced.

Also provided herein are isolated antibodies or antigen-binding fragments thereof that are produced by any method provided herein.

Also provided herein are pharmaceutical compositions comprising any antibody or antigen-binding fragment thereof provided herein and a pharmaceutically acceptable excipient.

Also provided herein are methods for detecting TTR in a sample comprising contacting the sample with any antibody or antigen-binding fragment thereof provided herein.

Also provided herein are methods of precipitating TTR from a sample comprising contacting the sample with any antibody or antigen-binding fragment thereof provided herein. In one aspect, the sample is obtained from a subject suspected of having a TTR amyloidosis.

Also provided herein are methods for increasing the uptake of TTR aggregates by an immune cell exposed to TTR aggregates comprising contacting the immune cell with any antibody or antigen-binding fragment provided herein or any pharmaceutical composition provided herein. In one aspect, the immune cell is a monocyte. In one aspect, the immune cell is a microglia.

Also provided herein are methods for decreasing the toxicity of TTR aggregates on a cell exposed to TTR aggregates comprising contacting the cell with any antibody or antigen-binding fragment thereof provided herein or any pharmaceutical composition provided herein. In one aspect, the cell is a cardiomyocyte.

Also provided herein are methods of inhibiting the accumulation of TTR aggregates in an organ exposed to TTR aggregates comprising contacting the organ with any antibody or antigen-binding fragment thereof provided herein or any pharmaceutical composition provided herein. In one aspect, the organ is a heart. In one aspect, the organ is a kidney. In one aspect, the contacting occurs in vitro. In one aspect, the contacting occurs in a subject.

Also provided herein are methods of treating or preventing a TTR amyloidosis in a subject comprising administering to the subject any antibody or antigen-binding fragment thereof provided herein or any pharmaceutical composition provided herein. In one aspect, the TTR amyloidosis is TTR-Familial Amyloidotic Polyneuropathy (FAP). In one aspect, the TTR amyloidosis is TTR-Familial Amyloidotic Cardiomyopathy (FAC). In one aspect, the TTR amyloidosis is TTR amyloid cardiomyopathy. In one aspect, the TTR amyloidosis is wild-type (WT) TTR amyloidosis.

Also provided herein are methods for detecting TTR in a subject comprising administering to the subject any antibody or antigen-binding fragment thereof provided herein or any pharmaceutical composition provided herein.

Also provided herein are methods for diagnosing a TTR amyloidosis in a subject comprising administering to the subject any antibody or antigen-binding fragment thereof provided herein or any pharmaceutical composition provided herein. In one aspect, the antibody or antigen-binding fragment thereof is linked to a detection reagent, optionally wherein the detection reagent is biotin, horse radish peroxidase (HRP), Cy5, FITC/Cy3, Alexa-488, or alkaline phosphatase.

In one aspect, the subject is a human.

Also provided herein are kits comprising any antibody or antigen-binding fragment thereof provided herein or any pharmaceutical composition provided herein and a) a detection reagent, b) TTR antigen, c) a notice that reflects approval for use or sale for human administration, or d) a combination thereof.

Also provided herein are methods for testing the activity of a TTR-binding compound comprising administering the TTR-binding compound and TTR fibrils to a rodent. In one aspect, the TTR fibrils are administered by injecting the TTR fibrils into an organ of the rodent. In one aspect, the organ is a heart. In one aspect, the organ is a kidney. In one aspect, the organ is a brain. In one aspect, the TTR-binding compound is administered after the TTR fibrils are injected. In one aspect, the TTR-binding compound is administered before the TTR fibrils are injected. In one aspect, the TTR-binding compound is administered with the TTR fibrils. In one aspect, the TTR fibrils are administered with a gelatinous protein mixture secreted by Engelbreth-Holm-Swarm (EHS) mouse sarcoma cells. In one aspect, the methods further comprise administering technetium pyrophosphate ($^{99m}$Tc-PYP) to the rodent after injection of the TTR fibrils. In one aspect, the $^{99m}$Tc-PYP is administered intravenously. In one aspect, the methods further comprise detecting the TTR fibrils and/or the $^{99m}$Tc-PYP. In one aspect, the TTR fibrils and/or $^{99m}$Tc-PYP is detected in the rodent. In one aspect, the TTR fibrils and/or $^{99m}$Tc-PYP is detected in an organ that has been removed from the rodent. In one aspect, the $^{99m}$Tc-PYP is detected using Computer tomography (CT) scanning. In one aspect, the rodent is a rat. In one aspect, the rat is a Sprague-Dawley rat.

BRIEF DESCRIPTION OF THE DRAWINGS/FIGURES

FIG. 3 is a table showing the binding of CGX304 to monomer and fibrillar TTR as measured by surface plasmon resonance (Biacore). "Ka" refers to the associate rate constant; "kd" refers to the dissociate rate constant; and "KD" refers to the affinity constant. (See Example 2.)

Figure 8B:
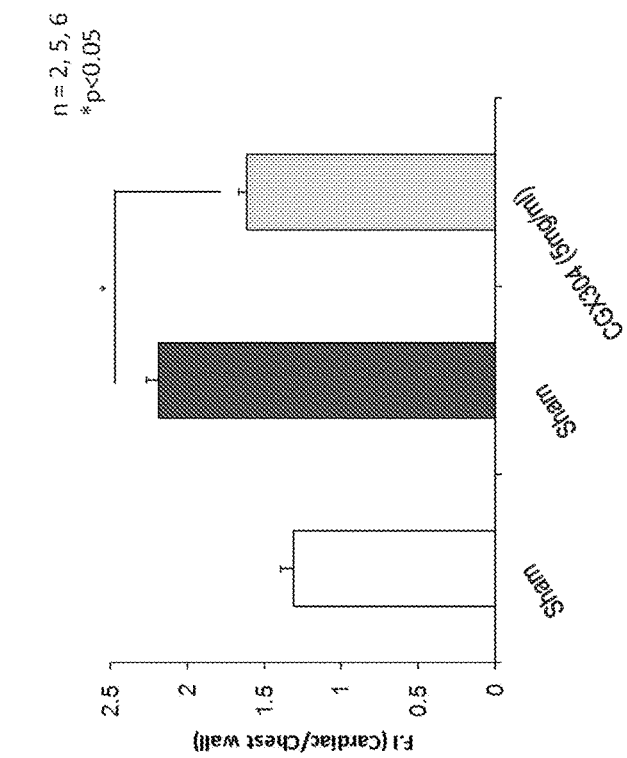
Figure 8A:
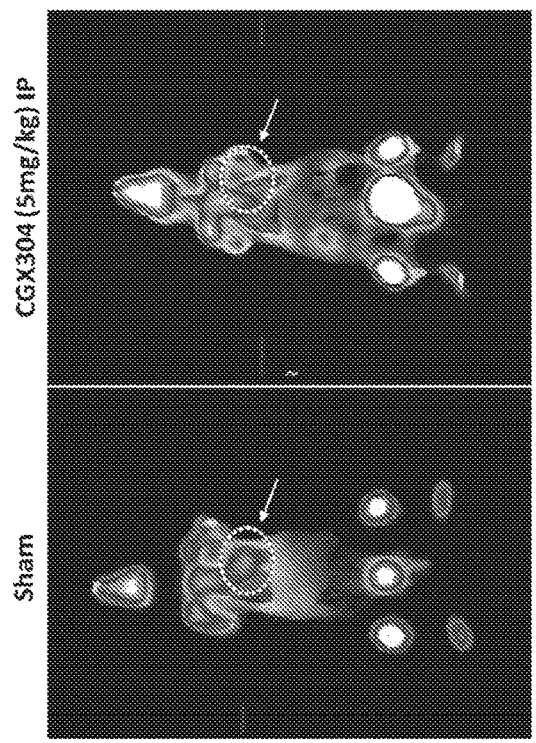

FIG. 8A shows aggregated TTR detected in rodents by PYP scans combined with Computer CT. TTR was injected into the rodents' hearts. The rodent in the left panel was treated with sham, and the rodent in the right panel was treated with CGX304. The white arrows indicate aggregated TTR as seen in PET-CT images. (See Example 7.)

FIG. 8B is a bar graph showing data from image analysis of CT scans quantitating fluorescence intensity (F.I) levels in rodents that received TTR injections in the heart and then treatment with either CGX304 or sham. The y-axis represents the F.I of the heart divided by the F.I of the chest wall used as background. (See Example 7.)

Figure 8C:
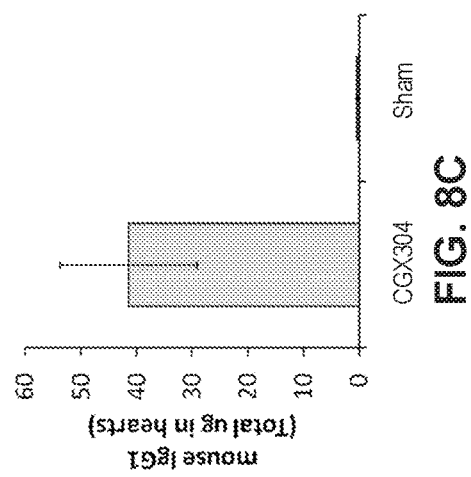

FIG. 8C is a bar graph showing CGX304 levels in the heart of rats post CT experiment. Mouse IgG1 levels were quantified using ELISA detection. The y-axis represents the change in mouse IgG1 levels. (See Example 7.)

Figure 9B:
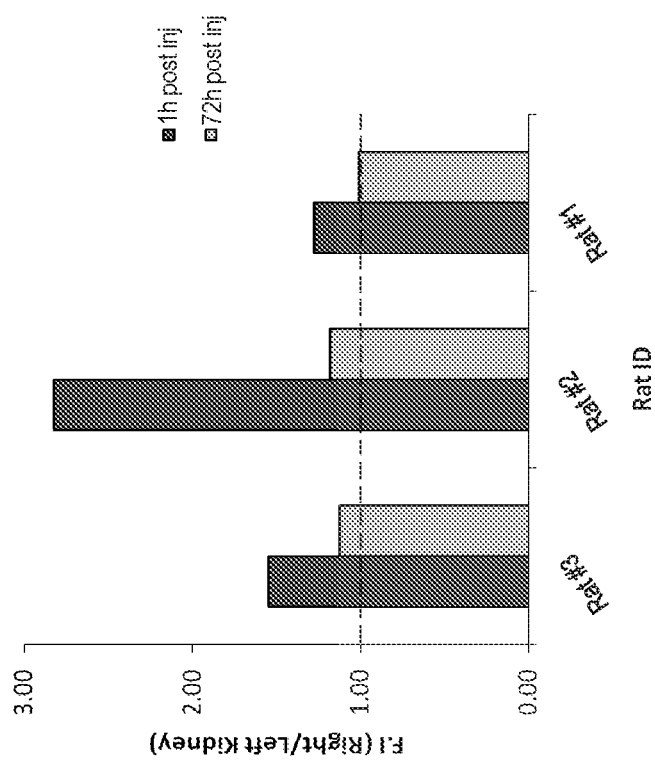
Figure 9C:
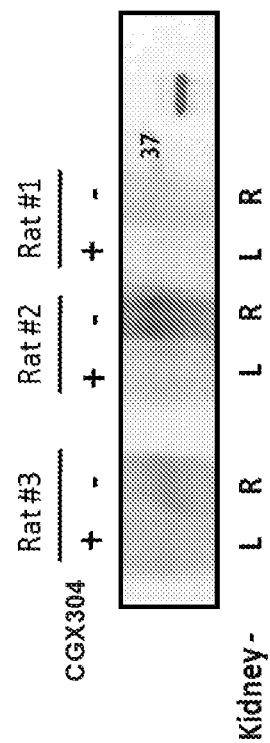
Figure 9A:
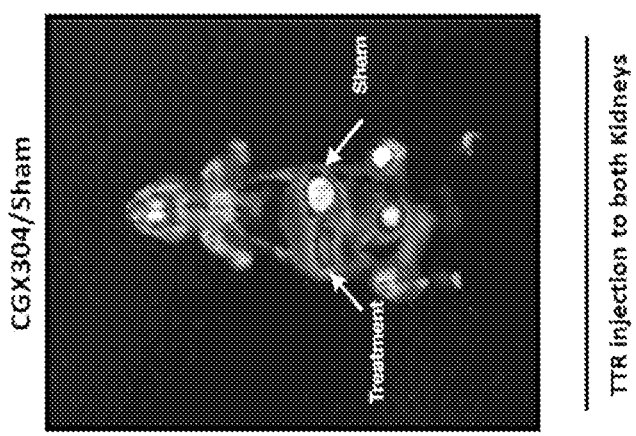

FIG. 9A shows aggregated TTR detected in a rodent by PET-CT. The rodent's left kidney was treated with CGX304, and the rodent's right kidney was treated with sham. (See Example 7.)

FIG. 9B is a bar graph showing data from image analysis of CT scans quantitating relative F.I levels of left and right kidneys of three rats that were treated with CGX304 in the left kidney and sham in the right kidney. The y-axis represents the F.I of the right kidney divided by the F.I of the left kidney. (See Example 7.)

FIG. 9C shows an image of a Western Blot showing TTR in CGX304-treated kidney compared to sham-treated kidney. (See Example 7.)

Figures 10A, 10B, 10C:
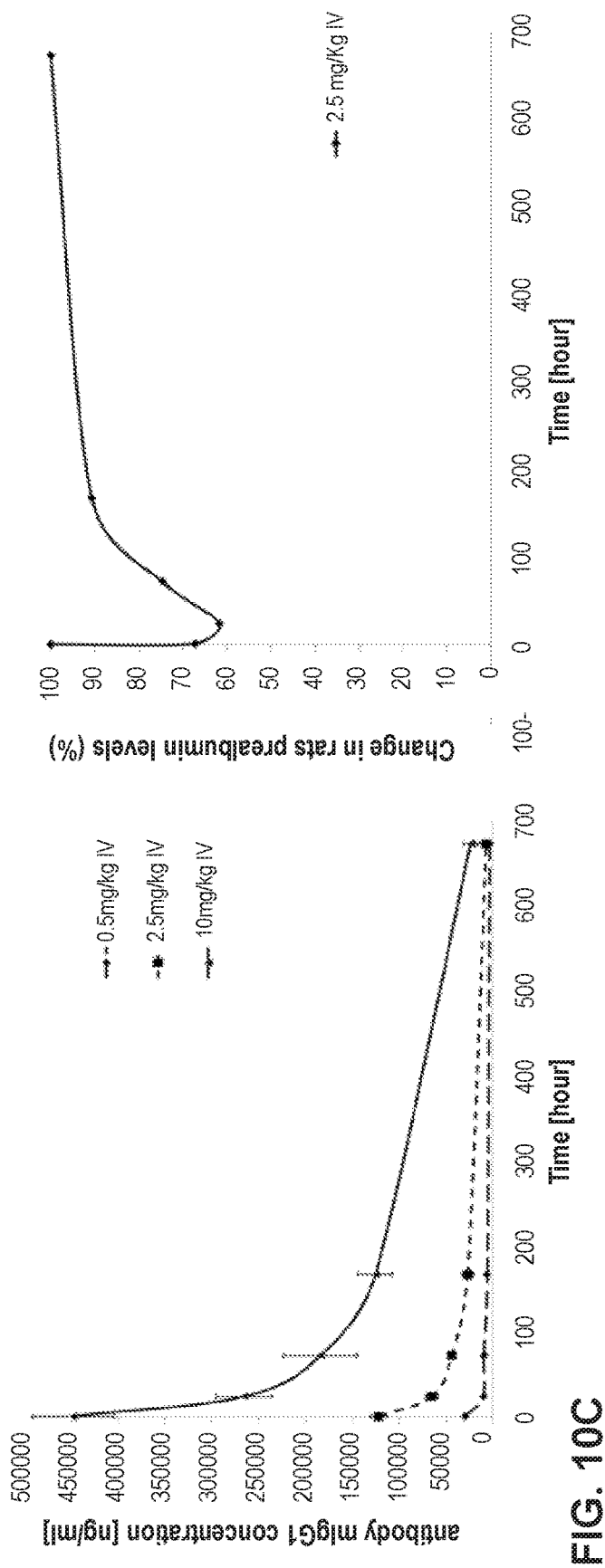

FIG. 10A is a graph showing the serum concentration of CGX304 over 28 days in animals that received intravenous ("IV") injections of 0.5 mg/kg, 2.5 mg/kg, or 10 mg/kg CGX304 (n=3, 3, 3). The y-axis represents the CGX304 concentration levels. (See Example 8.)

FIG. 10B is a graph showing the serum concentration of TTR over time in a rat that received an IV injection of 2.5 mg/kg CGX304. The y-axis represents the change in TTR levels. (See Example 8.)

FIG. 10C is a bar graph showing CGX304 levels in the heart of rats 28 days post IV treatment. CGX304 levels were quantified using ELISA detection assay. The y-axis represents the change in mouse IgG1 levels. (See Example 8.)

Figure 11:
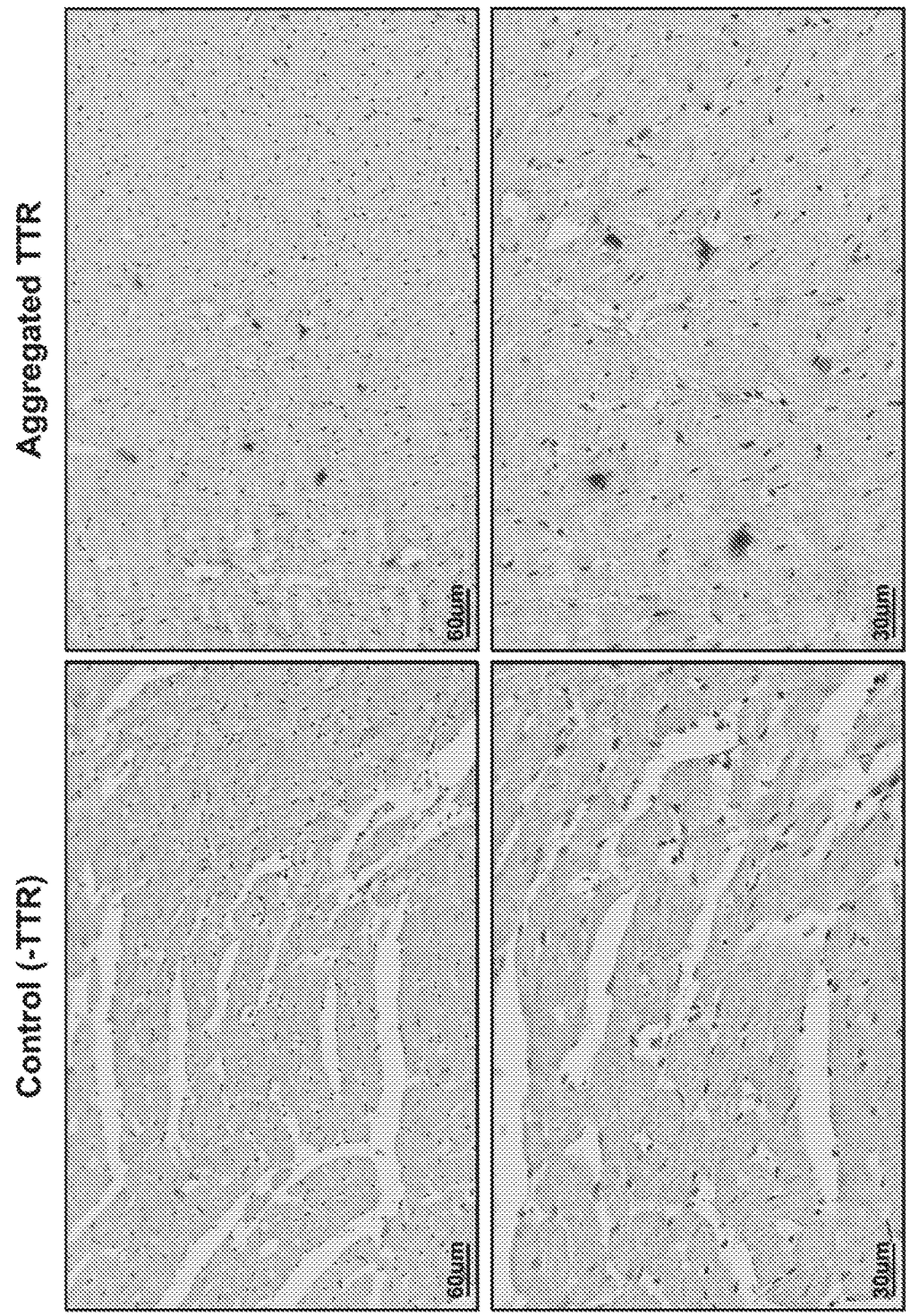

FIG. 11 is representative immunohistochemical staining images on rats injected with aggregated TTR (right panel) or control (sham animals injected with matrigel and no aggregated TTR—left panel) showing interstitial infiltration of aggregated TTR in the sections taken from mid and lower apical regions of respective rat hearts. (See Example 11.)

Figure 12:
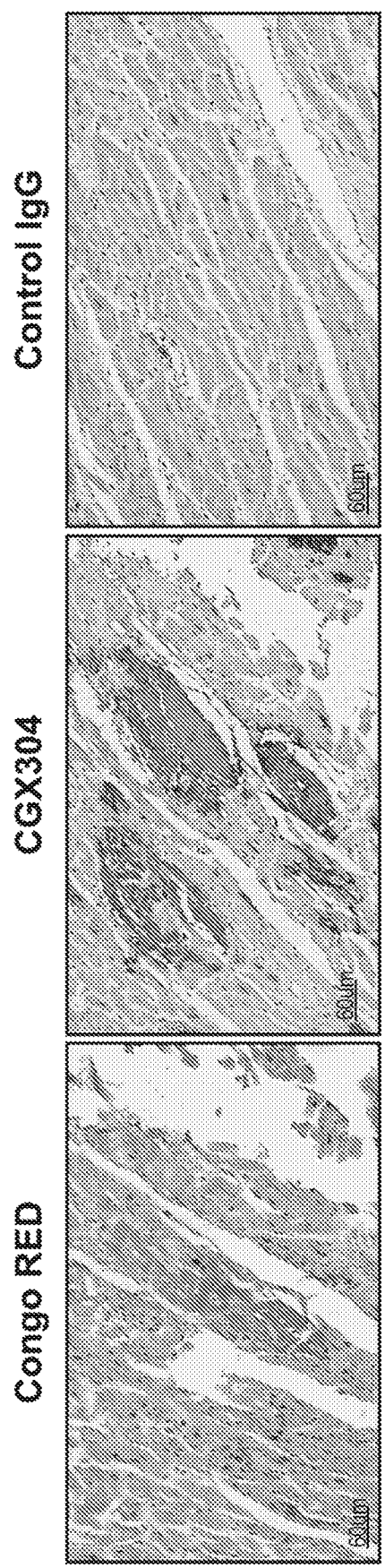

FIG. 12 shows immunohistochemical staining of a human heart tissue sample obtained from a TTR-amyloidosis patient using CGX304 (middle panel), isotype control IgG (right panel) and congo red staining (left panel) of the same human heart tissue sample. (See Example 9.)

Figure 13:
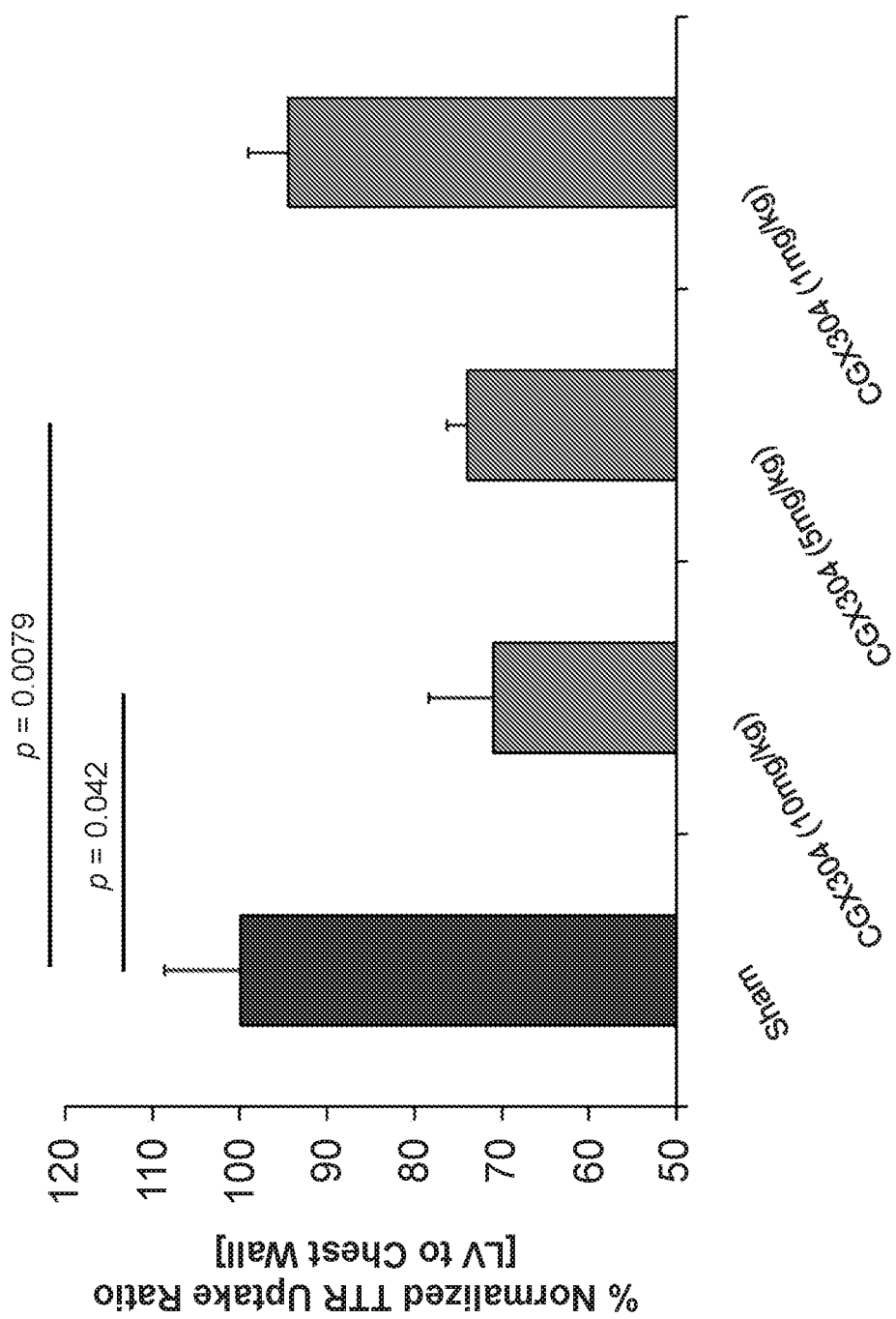

FIG. 13 is a bar graph showing data from image analysis of CT SPECT scans quantitating PYP uptake in rodents that received TTR injections in the heart and were then treated with either CGX304 or sham. The y-axis represents the left ventricle uptake divided by the chest wall uptake used as background. Error bars indicate SEM. (See Example 10.)

Figure 14C:
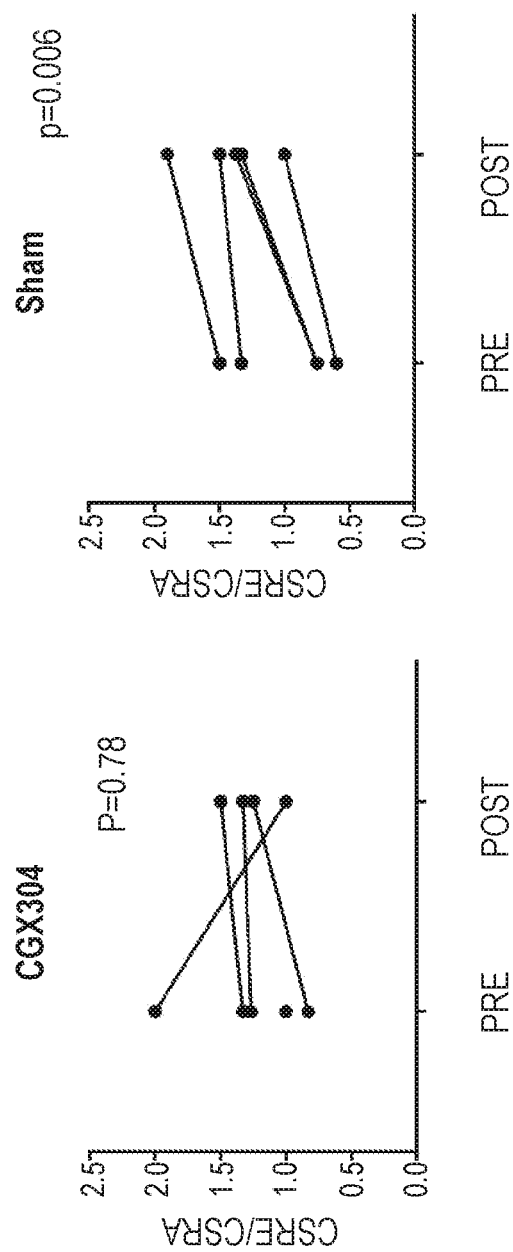
Figure 14D:
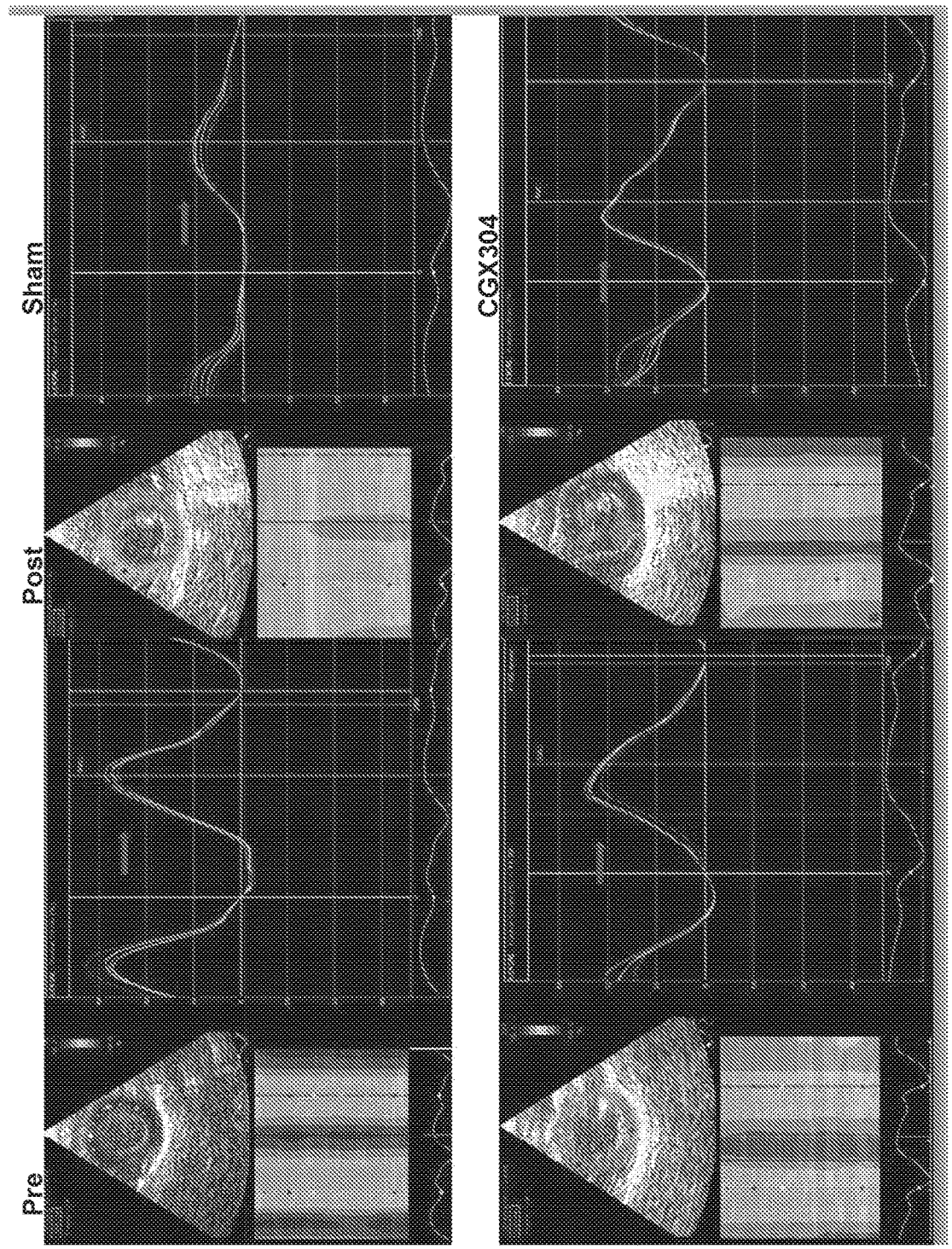
Figure 14E:
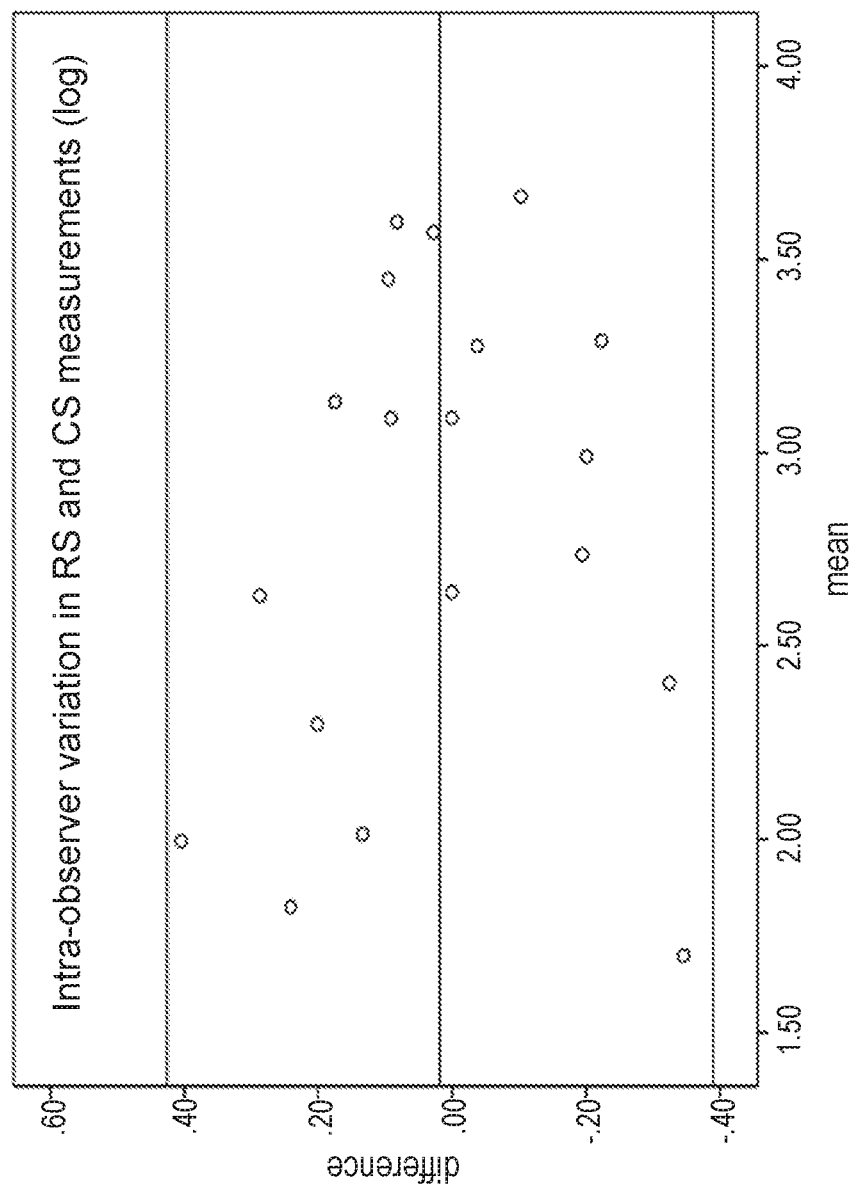

FIGS. 14A-14E show deformation indices measured before and after injection of TTR with and without CGX304. FIG. 14A shows the radial strain change in the two groups. FIG. 14B shows the circumferential strain rate S change in the two groups. FIG. 14C shows the ratio circumferential strain rate E to A in the two groups. FIG. 14D shows the myocardial radial strain before and after TTR injection with and without CGX304 treatment. The upper panel shows a decrease in Radial strain after injection of TTR. The lower panel shows no significant change in radial strain after injection of TTR and CGX304. FIG. 14E shows Band-Altman analysis of intra-observer variability in RS and CS measurements. (See Example 12.)

Figure 15:
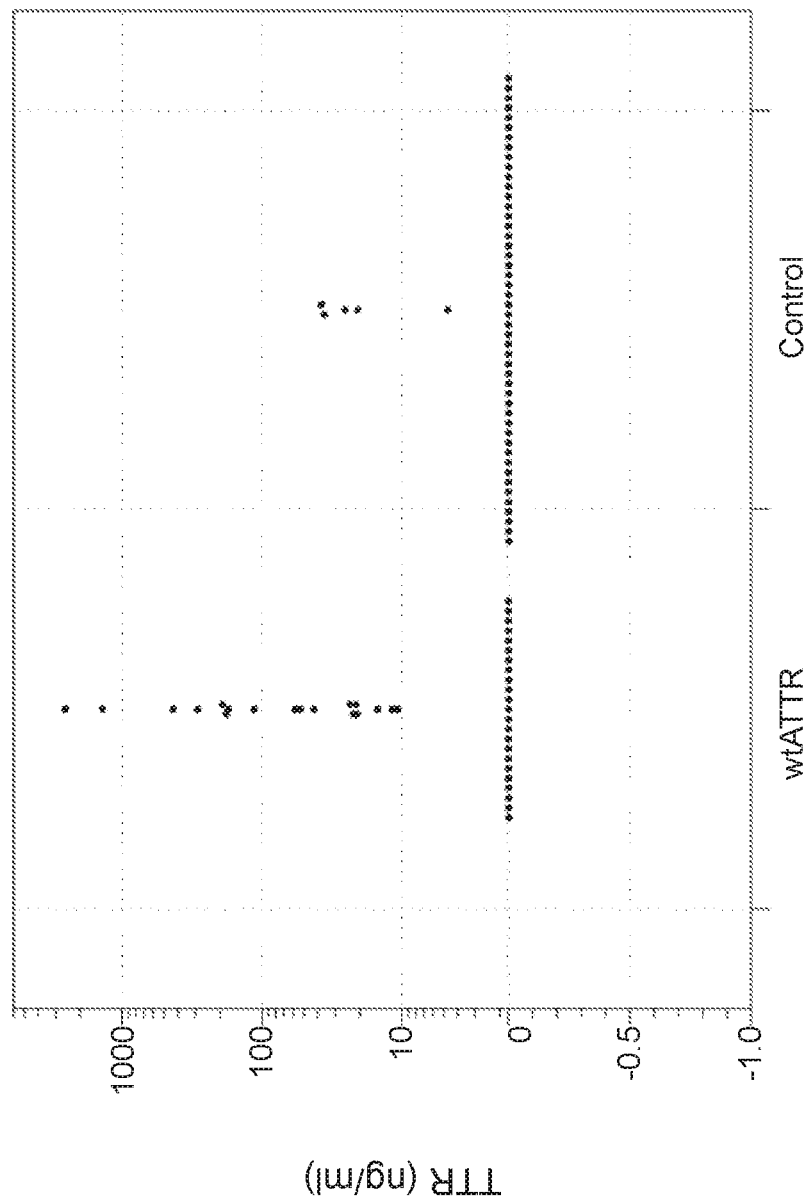

FIG. 15 shows the results of ELISA assay testing in the presence of circulating aggregated TTR employing CGX304 in the sera of patients with wild-type (wt) ATTR cardiac amyloidosis. Samples were measured in triplicate. (See Example 13)

DETAILED DESCRIPTION OF THE INVENTION

I. Terminology

As used herein, the terms "transthyretin" and "TTR" are interchangeable and refer to mammalian TTR polypeptides including, but not limited to, wild-type and mutant TTR polypeptides. "TTR" encompasses full-length, unprocessed TTR polypeptides as well as forms of TTR polypeptides that result from processing within the cell. "TTR" encompasses polypeptides in monomeric, tetrameric, and fibrillar forms. As used herein, the term "human TTR" refers to a polypeptide comprising amino acids 21-147 of SEQ ID NO:7. A "TTR polynucleotide," "TTR nucleotide," or "TTR nucleic acid" refer to a polynucleotide encoding TTR.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or sub-classes (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain an antigen recognition site of an intact antibody (e.g., complementarity determining regions (CDRs) sufficient to bind antigen). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

The terms "anti-TTR antibody," "TTR antibody," and "antibody that binds to TTR" refer to an antibody that is capable of binding TTR (in monomeric, tetrameric, and/or fibrillar form) with sufficient affinity such that the antibody is useful as a diagnostic and/or therapeutic agent in targeting TTR. The extent of binding of an anti-TTR antibody to an unrelated, non-TTR protein can be less than about 10% of the binding of the antibody to TTR as measured, e.g., by a radioimmunoassay (MA).

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibodies or antigen-binding fragments thereof refers to such antibodies and antigen-binding fragments thereof made in any number of manners including but not limited to by hybridoma, phage selection, recombinant expression, and transgenic animals.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that CDRs of the light and heavy chains are primarily responsible for the interaction and specificity of the antibody with antigen. In certain aspects, the variable region is a human variable region. In certain aspects, the variable region comprises rodent or murine CDRs and human framework regions (FRs). In particular aspects, the variable region is a primate (e.g., non-human primate) variable region. In certain aspects, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR H1), amino acid positions 50 to 65 (CDR H2), and amino acid positions 95 to 102 (CDR H3). Using the Kabat numbering system, CDRs within an antibody light chain molecule are typically present at amino acid positions 24 to 34 (CDR L1), amino acid positions 50 to 56 (CDR L2), and amino acid positions 89 to 97 (CDR L3). In a specific aspect, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32...34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

As used herein, the terms "constant region" and "constant domain" are interchangeable and have their meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha ($\alpha$), delta ($\delta$), epsilon ($\epsilon$), gamma ($\gamma$), and mu ($\mu$), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$. Heavy chain amino acid sequences are well known in the art. In specific aspects, the heavy chain is a human heavy chain.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific aspects, the light chain is a human light chain.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the non-human CDR residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some aspects, a "humanized antibody" is a resurfaced antibody.

The term "human" antibody or antigen-binding fragment thereof means an antibody or antigen-binding fragment thereof having an amino acid sequence derived from a human immunoglobulin gene locus, where such antibody or antigen-binding fragment is made using any technique known in the art. This definition of a human antibody or antigen-binding fragment thereof includes intact or full-length antibodies and fragments thereof.

"Binding affinity" generally refers to the strength of the sum total of non-covalent interactions between a single binding site of a molecule (e.g., an antibody or antigen-binding fragment thereof) and its binding partner (e.g., an antigen). Unless indicated otherwise, as used herein, "binding affinity" refers to intrinsic binding affinity which reflects a 1:1 interaction between members of a binding pair (e.g., antibody or antigen-binding fragment thereof and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody or antigen-binding fragment thereof to an antigen, and $k_{off}$ refers to the dissociation of, e.g., an antibody or antigen-binding fragment thereof from an antigen. The $k_{on}$ and $k_{off}$ can be determined by techniques known to one of ordinary skill in the art, such as BIAcore® or KinExA.

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain aspects, the epitope to which an antibody or antigen-binding fragment thereof binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50 (Pt 4): 339-350; McPherson A (1990) Eur J Biochem 189: 1-23; Chayen N E (1997) Structure 5: 1269-1274; McPherson A (1976) J Biol Chem 251: 6300-6303). Antibody/antigen-binding fragment thereof: antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49 (Pt 1): 37-60; Bricogne G (1997) Meth Enzymol 276A: 361-423, ed Carter C W; Roversi P et al., (2000) Acta Crystallogr D Biol Crystallogr 56 (Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

A TTR antibody that "binds to the same epitope" as a reference TTR antibody refers to an antibody that binds to the same TTR amino acid residues as the reference TTR antibody. The ability of a TTR antibody to bind to the same epitope as a reference TTR antibody is determined by a hydrogen/deuterium exchange assay (see Coales et al. Rapid Commun. Mass Spectrom. 2009; 23: 639-647).

As used herein, the terms "immunospecifically binds," "immunospecifically recognizes," "specifically binds," and "specifically recognizes" are analogous terms in the context of antibodies or antigen-binding fragments thereof. These terms indicate that the antibody or antigen-binding fragment thereof binds to an epitope via its antigen-binding domain and that the binding entails some complementarity between the antigen-binding domain and the epitope. Accordingly, an antibody that "specifically binds" to human TTR (amino acids 21-147 of SEQ ID NO:7) may also bind to TTR from other species (e.g., cynomolgus monkey, mouse, and/or rat TTR) and/or TTR proteins produced from other human alleles, but the extent of binding to an un-related, non-TTR protein is less than about 10% of the binding of the antibody to TTR as measured, e.g., by a radioimmunoassay (MA).

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition can be determined by any method known in the art, for example, competition ELISA assays. An antibody may be said to competitively inhibit binding of the reference antibody to a given epitope by at least 90%, at least 80%, at least 70%, at least 60%, or at least 50%.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some aspects, an antibody, polynucleotide, vector, cell, or composition which is isolated is substantially pure. As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain aspects, the polypeptides can occur as single chains or associated chains.

"Percent identity" refers to the extent of identity between two sequences (e.g., amino acid sequences or nucleic acid sequences). Percent identity can be determined by aligning two sequences, introducing gaps to maximize identity between the sequences. Alignments can be generated using programs known in the art. For purposes herein, alignment of nucleotide sequences can be performed with the blastn program set at default parameters, and alignment of amino acid sequences can be performed with the blastp program set at default parameters (see National Center for Biotechnology Information (NCBI) on the worldwide web, ncbi.nlm.nih.gov).

As used herein, the term "host cell" can be any type of cell, e.g., a primary cell, a cell in culture, or a cell from a cell line. In specific aspects, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The terms "administer," "administering," "administration," and the like, as used herein, refer to methods that may be used to enable delivery of a drug, e.g., an anti-TTR antibody or antigen-binding fragment thereof to the desired site of biological action (e.g., intravenous administration). Administration techniques that can be employed with the agents and methods described herein are found in e.g., Goodman and Gilman, *The Pharmacological Basis of Therapeutics*, current edition, Pergamon; and Remington's, *Pharmaceutical Sciences*, current edition, Mack Publishing Co., Easton, Pa.

As used herein, the terms "subject" and "patient" are used interchangeably. The subject can be an animal. In some aspects, the subject is a mammal such as a non-human animal (e.g., cow, pig, horse, cat, dog, rat, mouse, monkey or other primate, etc.). In some aspects, the subject is a human.

The term "therapeutically effective amount" refers to an amount of a therapeutic, e.g., an anti-TTR antibody or antigen-binding fragment thereof, effective to treat a disease or disorder in a subject. In the case of TTR amyloidosis, the therapeutically effective amount of the therapeutic can reduce the number and/or size of amyloid fibrils, attenuate polyneuropathy, attenuate and/or improve symptoms in patients with ATTR-related heart failure, and/or decrease cardiomyopathy. A "prophylactically effective amount" refers to an amount effective to achieve the desired prophylactic result.

Terms such as "treating," "treatment," "to treat," "alleviating," and "to alleviate" refer to therapeutic measures that cure, slow down, lessen symptoms of, and/or halt progression of a pathologic condition or disorder. Thus, those in need of treatment include those already diagnosed with or suspected of having the disorder. In certain aspects, a subject is successfully "treated" for a TTR amyloidosis according to the methods of the present invention if the patient shows one or more of the following: reduce the number of amyloid fibrils, decrease polyneuropathy, and/or decrease cardiomyopathy.

Prophylactic or preventative measures refer to measures that prevent and/or slow the development of a targeted pathological condition or disorder, e.g., a TTR amyloidosis. Thus, those in need of prophylactic or preventative measures include those prone to have the pathological condition or disorder and those in whom the pathological condition or disorder is to be prevented.

The term "TTR amyloidosis" refers to a condition characterized by the buildup of abnormal deposits of amyloid (amyloidosis) in the body's organs and tissues (e.g., the nervous system, cardiac tissue, kidneys and/or other organs). TTR amyloidosis includes neuropathic TTR amyloidosis, leptomeningeal TTR amyloidosis, renal amyloidosis and cardiac TTR amyloidosis.

As used in the present disclosure and claims, the singular forms "a," "an," and "the" include plural forms unless the context clearly dictates otherwise.

It is understood that wherever aspects are described herein with the language "comprising," otherwise analogous aspects described in terms of "consisting of" and/or "consisting essentially of" are also provided. In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited are not changed by the presence of more than that which is recited, but excludes prior art embodiments.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "about" and "approximately," when used to modify a numeric value or numeric range, indicate that deviations of 5% to 10% above and 5% to 10% below the value or range remain within the intended meaning of the recited value or range.

Any compositions or methods provided herein can be combined with one or more of any of the other compositions and methods provided herein

II. Anti-Transthyretin (TTR) Antibodies and Antigen-Binding Fragments Thereof In a specific aspect, provided herein are antibodies (e.g., monoclonal antibodies) and antigen-binding fragments thereof which specifically bind to transthyretin (TTR) (e.g., human TTR). The amino acid sequences for human TTR are known in the art and are also provided herein as amino acids 24-147 of SEQ ID NO:7.

Human TTR:

(SEQ ID NO: 7)
<u>MASHRLLLLCLAGLVFVSEAGPTGTGESKCPLMVKVLDAVRGSPAINVA</u>

VHVFRKAADDTWEPFASGKTSESGELHGLTTEEEFVEGIYKVEIDTKSY

WKALGISPFHEHAEVVFTANDSGPRRYTIAALLSPYSYSTTAVVTNPKE (The underlined amino acids (amino acids 1-20) of SEQ ID NO:7 are the signal sequence of human TTR.)

In certain aspects, an antibody or antigen-binding fragment thereof for use in the methods described herein binds to human TTR and comprises the six CDRs of the CGX304 antibody listed as provided in Tables 1 and 2.

TABLE 1

| | VH CDR Amino Acid Sequences | | |
|---|---|---|---|
| Antibody | CDR H1 (SEQ ID NO:) | CDR H2 (SEQ ID NO:) | CDR H3 (SEQ ID NO:) |
| CGX304-IMGT defined | GYTFTSYY (SEQ ID NO: 1) | IYPGNVNT (SEQ ID NO: 2) | ARTYFDY (SEQ ID NO: 3) |
| CGX304-Kabat defined | SYYIH (SEQ ID NO: 8) | WIYPGNVNT KYNEKFKG (SEQ ID NO: 9) | TYFDY (SEQ ID NO: 10) |

TABLE 2

VL CDR Amino Acid Sequences

| Antibody | CDR L1 (SEQ ID NO:) | CDR L2 (SEQ ID NO:) | CDR L3 (SEQ ID NO:) |
|---|---|---|---|
| CGX304 - IMGT defined | SSVSY (SEQ ID NO: 4) | DTS (SEQ ID NO: 5) | QQWSSKSFT (SEQ ID NO: 6) |
| CGX304 - Kabat defined | SASSSVSYMH (SEQ ID NO: 11) | DTSKLAS (SEQ ID NO: 12) | QQWSSKSFT (SEQ ID NO: 6) |

In certain aspects, an antibody or antigen-binding fragment thereof described herein binds to human TTR and comprises a VH comprising the same amino acid sequence as the VH of the antibody produced by the hybridoma cell line deposited at the American Type Culture Collection (ATCC®) at 10801 University Blvd Manassas, Virginia, 20110 USA as deposit number PTA-125005 on Mar. 14, 2018, e.g., in combination with a VL.

In certain aspects, an antibody or antigen-binding fragment thereof described herein binds to human TTR and comprises a VL comprising the same amino acid sequence as the VL of the antibody produced by the hybridoma of ATCC® depositPTA-125005, e.g., in combination with a VH.

In certain aspects, an antibody or antigen-binding fragment thereof described herein binds to human TTR and comprises a VH comprising the same amino acid sequence as the VH of the antibody produced by the hybridoma of ATCC® deposit number PTA-125005, and a VL comprising the same amino acid sequence as the VL of the antibody produced by the hybridoma of ATCC® deposit number PTA-125005.

In certain aspects, an antibody or antigen-binding fragment thereof described herein binds to human TTR, comprises a VH comprising a sequence at least 80% identical to the VH of the antibody produced by the hybridoma of ATCC® deposit number PTA-125005, and a VL comprising a sequence at least 80% identical to the VL of the antibody produced by the hybridoma of ATCC® deposit number PTA-125005. In certain aspects, an antibody or antigen-binding fragment thereof described herein binds to human TTR, comprises a VH comprising a sequence at least 85% identical to the VH of the antibody produced by the hybridoma of ATCC® deposit number PTA-125005, and a VL comprising a sequence at least 85% identical to the VL of the antibody produced by the hybridoma of ATCC® deposit number PTA-125005.

In certain aspects, an antibody or antigen-binding fragment thereof described herein binds to human TTR, comprises a VH comprising a sequence at least 90% identical to the VH of the antibody produced by the hybridoma of ATCC® deposit number PTA-125005, and a VL comprising a sequence at least 90% identical to the VL of the antibody produced by the hybridoma of ATCC® deposit number PTA-125005. In certain aspects, an antibody or antigen-binding fragment thereof described herein binds to human TTR, comprises a VH comprising a sequence at least 95% identical to the VH of the antibody produced by the hybridoma of ATCC® deposit number PTA-125005, and a VL comprising a sequence at least 95% identical to the VL of the antibody produced by the hybridoma of ATCC® deposit number PTA-125005.

In certain aspects, an antibody or antigen-binding fragment thereof described herein binds to human TTR, comprises a VH comprising a sequence at least 96% identical to the VH of the antibody produced by the hybridoma of ATCC® deposit number PTA-125005, and a VL comprising a sequence at least 96% identical to the VL of the antibody produced by the hybridoma of ATCC® deposit number PTA-125005. In certain aspects, an antibody or antigen-binding fragment thereof described herein binds to human TTR, comprises a VH comprising a sequence at least 97% identical to the VH of the antibody produced by the hybridoma of ATCC® deposit number PTA-125005, and a VL comprising a sequence at least 97% identical to the VL of the antibody produced by the hybridoma of ATCC® deposit number PTA-125005. In certain aspects, an antibody or antigen-binding fragment thereof described herein binds to human TTR, comprises a VH comprising a sequence at least 98% identical to the VH of the antibody produced by the hybridoma of ATCC® deposit number PTA-125005, and a VL comprising a sequence at least 98% identical to the VL of the antibody produced by the hybridoma of ATCC® deposit number PTA-125005. In certain aspects, an antibody or antigen-binding fragment thereof described herein binds to human TTR, comprises a VH comprising a sequence at least 99% identical to the VH of the antibody produced by the hybridoma of ATCC® deposit number PTA-125005, and a VL comprising a sequence at least 99% identical to the VL of the antibody produced by the hybridoma of ATCC® deposit number PTA-125005.

In certain aspects, an antibody or antigen-binding fragment thereof described herein binds to human TTR, comprises a VH comprising a sequence at least 80% identical to the VH of the antibody produced by the hybridoma of ATCC® deposit number PTA-125005, and a VL comprising a sequence at least 80% identical to the VL of the antibody produced by the hybridoma of ATCC® deposit number PTA-125005, wherein the antibody or antigen-binding fragment thereof decreases the toxicity of TTR fibrils (e.g., on human cardiomyocytes). In certain aspects, an antibody or antigen-binding fragment thereof described herein binds to human TTR, comprises a VH comprising a sequence at least 85% identical to the VH of the antibody produced by the hybridoma of ATCC® deposit number PTA-125005, and a VL comprising a sequence at least 85% identical to the VL of the antibody produced by the hybridoma of ATCC® deposit number PTA-125005, wherein the antibody or antigen-binding fragment thereof decreases the toxicity of TTR fibrils (e.g., on human cardiomyocytes).

In certain aspects, an antibody or antigen-binding fragment thereof described herein binds to human TTR, comprises a VH comprising a sequence at least 90% identical to the VH of the antibody produced by the hybridoma of ATCC® deposit number PTA-125005, and a VL comprising a sequence at least 90% identical to the VL of the antibody produced by the hybridoma of ATCC® deposit number PTA-125005, wherein the antibody or antigen-binding fragment thereof decreases the toxicity of TTR fibrils (e.g., on human cardiomyocytes). In certain aspects, an antibody or antigen-binding fragment thereof described herein binds to human TTR, comprises a VH comprising a sequence at least 95% identical to the VH of the antibody produced by the hybridoma of ATCC® deposit number PTA-125005, and a VL comprising a sequence at least 95% identical to the VL of the antibody produced by the hybridoma of ATCC® deposit number PTA-125005, wherein the antibody or antigen-binding fragment thereof decreases the toxicity of TTR fibrils (e.g., on human cardiomyocytes).

In certain aspects, an antibody or antigen-binding fragment thereof described herein binds to human TTR, comprises a VH comprising a sequence at least 96% identical to the VH of the antibody produced by the hybridoma of ATCC® deposit number PTA-125005, and a VL comprising a sequence at least 96% identical to the VL of the antibody produced by the hybridoma of ATCC® deposit number PTA-125005, wherein the antibody or antigen-binding fragment thereof decreases the toxicity of TTR fibrils (e.g., on human cardiomyocytes). In certain aspects, an antibody or antigen-binding fragment thereof described herein binds to human TTR, comprises a VH comprising a sequence at least 97% identical to the VH of the antibody produced by the hybridoma of ATCC® deposit number PTA-125005, and a VL comprising a sequence at least 97% identical to the VL of the antibody produced by the hybridoma of ATCC® deposit number PTA-125005, wherein the antibody or antigen-binding fragment thereof decreases the toxicity of TTR fibrils (e.g., on human cardiomyocytes). In certain aspects, an antibody or antigen-binding fragment thereof described herein binds to human TTR, comprises a VH comprising a sequence at least 98% identical to the VH of the antibody produced by the hybridoma of ATCC® deposit number PTA-125005, and a VL comprising a sequence at least 98% identical to the VL of the antibody produced by the hybridoma of ATCC® deposit number PTA-125005, wherein the antibody or antigen-binding fragment thereof decreases the toxicity of TTR fibrils (e.g., on human cardiomyocytes). In certain aspects, an antibody or antigen-binding fragment thereof described herein binds to human TTR, comprises a VH comprising a sequence at least 99% identical to the VH of the antibody produced by the hybridoma of ATCC® deposit number PTA-125005, and a VL comprising a sequence at least 99% identical to the VL of the antibody produced by the hybridoma of ATCC® deposit number PTA-125005, wherein the antibody or antigen-binding fragment thereof decreases the toxicity of TTR fibrils (e.g., on human cardiomyocytes).

In certain aspects, an antibody or antigen-binding fragment thereof described herein binds to human TTR, comprises a VH comprising a sequence at least 80% identical to the VH of the antibody produced by the hybridoma of ATCC® deposit number PTA-125005, and a VL comprising a sequence at least 80% identical to the VL of the antibody produced by the hybridoma of ATCC® deposit number PTA-125005, wherein the antibody or antigen-binding fragment thereof inhibits accumulation of TTR aggregates (e.g., in an organ such as a heart and/or kidney). In certain aspects, an antibody or antigen-binding fragment thereof described herein binds to human TTR, comprises a VH comprising a sequence at least 85% identical to the VH of the antibody produced by the hybridoma of ATCC® deposit number PTA-125005, and a VL comprising a sequence at least 85% identical to the VL of the antibody produced by the hybridoma of ATCC® deposit number PTA-125005, wherein the antibody or antigen-binding fragment thereof inhibits accumulation of TTR aggregates (e.g., in an organ such as a heart and/or kidney).

In certain aspects, an antibody or antigen-binding fragment thereof described herein binds to human TTR, comprises a VH comprising a sequence at least 90% identical to the VH of the antibody produced by the hybridoma of ATCC® deposit number PTA-125005, and a VL comprising a sequence at least 90% identical to the VL of the antibody produced by the hybridoma of ATCC® deposit number PTA-125005, wherein the antibody or antigen-binding fragment thereof inhibits accumulation of TTR aggregates (e.g., in an organ such as a heart and/or kidney). In certain aspects, an antibody or antigen-binding fragment thereof described herein binds to human TTR, comprises a VH comprising a sequence at least 95% identical to the VH of the antibody produced by the hybridoma of ATCC® deposit number PTA-125005, and a VL comprising a sequence at least 95% identical to the VL of the antibody produced by the hybridoma of ATCC® deposit number PTA-125005, wherein the antibody or antigen-binding fragment thereof inhibits accumulation of TTR aggregates (e.g., in an organ such as a heart and/or kidney).

In certain aspects, an antibody or antigen-binding fragment thereof described herein binds to human TTR, comprises a VH comprising a sequence at least 96% identical to the VH of the antibody produced by the hybridoma of ATCC® deposit number PTA-125005, and a VL comprising a sequence at least 96% identical to the VL of the antibody produced by the hybridoma of ATCC® deposit number PTA-125005, wherein the antibody or antigen-binding fragment thereof inhibits accumulation of TTR aggregates (e.g., in an organ such as a heart and/or kidney). In certain aspects, an antibody or antigen-binding fragment thereof described herein binds to human TTR, comprises a VH comprising a sequence at least 97% identical to the VH of the antibody produced by the hybridoma of ATCC® deposit number PTA-125005, and a VL comprising a sequence at least 97% identical to the VL of the antibody produced by the hybridoma of ATCC® deposit number PTA-125005, wherein the antibody or antigen-binding fragment thereof inhibits accumulation of TTR aggregates (e.g., in an organ such as a heart and/or kidney). In certain aspects, an antibody or antigen-binding fragment thereof described herein binds to human TTR, comprises a VH comprising a sequence at least 98% identical to the VH of the antibody produced by the hybridoma of ATCC® deposit number PTA-125005, and a VL comprising a sequence at least 98% identical to the VL of the antibody produced by the hybridoma of ATCC® deposit number PTA-125005, wherein the antibody or antigen-binding fragment thereof inhibits accumulation of TTR aggregates (e.g., in an organ such as a heart and/or kidney). In certain aspects, an antibody or antigen-binding fragment thereof described herein binds to human TTR, comprises a VH comprising a sequence at least 99% identical to the VH of the antibody produced by the hybridoma of ATCC® deposit number PTA-125005, and a VL comprising a sequence at least 99% identical to the VL of the antibody produced by the hybridoma of ATCC® deposit number PTA-125005, wherein the antibody or antigen-binding fragment thereof inhibits accumulation of TTR aggregates (e.g., in an organ such as a heart and/or kidney).

In certain aspects, an antibody or antigen-binding fragment thereof described herein may be described by its VL domain alone or its VH domain alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352: 624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are antibodies and antigen-binding fragments thereof that specifically bind to TTR (e.g., human TTR) and comprise the Chothia VH and VL CDRs of an antibody. In certain aspects, antibodies or antigen-binding fragments thereof that specifically bind to TTR (e.g., human TTR) comprise one or more CDRs, in which the Chothia and Kabat CDRs have the same amino acid sequence. In certain aspects, provided herein are antibodies and antigen-binding fragments thereof that specifically bind to TTR (e.g., human TTR) and comprise combinations of Kabat CDRs and Chothia CDRs.

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, CDR H1 is at positions 26 to 35, CDR H2 is at positions 51 to 57, CDR H3 is at positions 93 to 102, CDR L1 is at positions 27 to 32, CDR L2 is at positions 50 to 52, and CDR L3 is at positions 89 to 97. In a particular aspect, provided herein are antibodies and antigen-binding fragments thereof that specifically bind to TTR (e.g., human TTR) and comprise the IMGT VH and VL CDRs of an antibody listed in Tables 3 and 4, for example, as described in Lefranc M-P (1999) supra and Lefranc M-P et al., (1999) supra).

In certain aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in Antibody Engineering, Kontermann and Dithel, eds., Chapter 31, pp. 422-439, Springer-Verlag, Berlin (2001). In a particular aspect, provided herein are antibodies or antigen-binding fragments thereof that specifically bind to TTR (e.g., human TTR) are determined by the method in MacCallum R M et al.

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular aspect, provided herein are antibodies or antigen-binding fragments thereof that specifically bind to TTR (e.g., human TTR) are determined by the AbM numbering scheme.

In certain aspects, an antibody or antigen-binding fragment thereof described herein binds to human TTR and comprises a heavy chain comprising the same amino acid sequence as the heavy chain of the antibody produced by the hybridoma of ATCC® deposit number PTA-125005, e.g., in combination with a light chain.

In certain aspects, an antibody or antigen-binding fragment thereof described herein binds to human TTR and comprises a light chain comprising the same amino acid sequence as the light chain of the antibody produced by the hybridoma of ATCC® deposit number PTA-125005, e.g., in combination with a heavy chain.

In certain aspects, an antibody or antigen-binding fragment thereof described herein binds to human TTR and comprises a heavy chain comprising the same amino acid sequence as the heavy chain of the antibody produced by the hybridoma of ATCC® deposit number PTA-125005, and a light chain comprising the same amino acid sequence as the light chain of the antibody produced by the hybridoma of ATCC® deposit number PTA-125005.

In specific aspects, provided herein are antibodies that comprise a heavy chain and alight chain.

In a specific aspect, the heavy chain of an antibody described herein is a gamma heavy chain (e.g., a human gamma heavy chain, e.g., human $IgG_1$ heavy chain). In a particular aspect, an antibody which immunospecifically binds to TTR (e.g., human TTR) provided herein comprises a heavy chain wherein the amino acid sequence of the VH domain comprises the VH sequence of the antibody produced by the hybridoma of ATCC® deposit number PTA-125005, and wherein the constant region of the heavy chain comprises the amino acid sequence of a human gamma heavy chain (e.g., human $IgG_1$ heavy chain) constant region.

In a specific aspect, the light chain of an antibody described herein is a kappa light chain (e.g., a human kappa light chain). In a particular aspect, an antibody which immunospecifically binds to TTR (e.g., human TTR) provided herein comprises a light chain wherein the amino acid sequence of the VL domain comprises the VL sequence of the antibody produced by the hybridoma of ATCC® deposit number PTA-125005, and wherein the constant region of the light chain comprises the amino acid sequence of a human kappa light chain constant region.

In a particular aspect, an antibody which immunospecifically binds to TTR (e.g., human TTR) provided herein comprises (i) a heavy chain wherein the amino acid sequence of the VH domain comprises the VH sequence of the antibody produced by the hybridoma of ATCC® deposit number PTA-125005, and wherein the constant region of the heavy chain comprises the amino acid sequence of a human gamma heavy chain (e.g., human $IgG_1$ heavy chain) constant region and (ii) comprises a light chain wherein the amino acid sequence of the VL domain comprises the VL sequence of the antibody produced by the hybridoma of ATCC® deposit number PTA-125005, and wherein the constant region of the light chain comprises the amino acid sequence of a human kappa light chain constant region.

In another particular aspect, an antibody or antigen-binding fragment thereof described herein, which immunospecifically binds to TTR (e.g., human TTR), comprises a heavy chain and a light chain, wherein (i) the heavy chain comprises a VH domain comprising the CDR H1, CDR H2, and CDR H3 amino acid sequences of the CGX304 antibody listed in Table 1; (ii) the light chain comprises a VL domain comprising the CDR L1, CDR L2, and CDR L3 amino acid sequences of the CGX304 antibody listed in Table 2; (iii) the heavy chain further comprises a constant heavy chain domain comprising the amino acid sequence of the constant domain of a human $IgG_1$ heavy chain; and (iv) the light chain further comprises a constant light chain domain comprising the amino acid sequence of the constant domain of a human kappa light chain.

In another aspect, provided herein are antibody or antigen-binding fragments thereof that specifically bind to TTR and decreases the toxicity of TTR fibrils (e.g., on human cardiomyocytes). In another aspect, provided herein are antibodies or antigen-binding fragments thereof that specifically bind to TTR and inhibit accumulation of TTR aggregates in an organ. The organ can be, for example, a heart and/or a kidney.

In another aspect, provided herein are antibodies or antigen-binding fragments thereof that bind the same epitope of TTR (e.g., an epitope of human TTR) as CGX304.

Competition binding assays can be used to determine whether two antibodies bind to overlapping epitopes. Competitive binding can be determined in an assay in which the immunoglobulin under test inhibits specific binding of a reference antibody to a common antigen, such as TTR. Numerous types of competitive binding assays are known, for example: solid phase direct or indirect radioimmunoassay (MA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using I-125 label (see Morel G A et al., (1988) Mol Immunol 25(1): 7-15); solid phase direct biotin-avidin EIA (Cheung R C et al., (1990) Virology 176: 546-52); and direct labeled MA. (Moldenhauer G et al., (1990) Scand J Immunol 32: 77-82). Typically, such an assay involves the use of purified antigen (e.g., TTR such as human TTR) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In one aspect, a competition assay is performed using surface plasmon resonance (BIAcore®), e.g., by an 'in tandem approach' such as that described by Abdiche Y N et al., (2009) Analytical Biochem 386: 172-180, whereby TTR antigen is immobilized on the chip surface, for example, a CMS sensor chip and the anti-TTR antibodies are then run over the chip. To determine if an antibody or antigen-binding fragment thereof competes with an anti-TTR antibody described herein, the anti-TTR antibody is first run over the chip surface to achieve saturation and then the potential, competing antibody is added. Binding of the competing antibody or antigen-binding fragment thereof can then be determined and quantified relative to a non-competing control.

In one aspect, provided herein are antibodies that competitively inhibit (e.g., in a dose dependent manner) CGX304 from binding to TTR (e.g., human TTR), as determined using assays known to one of skill in the art or described herein (e.g., ELISA competitive assays, or suspension array or surface plasmon resonance assay).

In specific aspects, provided herein is an antibody or antigen-binding fragment which competitively inhibits (e.g., in a dose dependent manner) binding to TTR (e.g., human TTR), of an antibody comprising the VH sequence of the antibody produced by the hybridoma of ATCC® deposit number PTA-125005, and the VL sequence of the antibody produced by the hybridoma of ATCC® deposit number PTA-125005.

In a specific aspect, an antigen-binding fragment as described herein, which immunospecifically binds to TTR (e.g., human TTR), is selected from the group consisting of a Fab, Fab', F(ab')$_2$, and scFv, wherein the Fab, Fab', F(ab')$_2$, or scFv comprises a heavy chain variable region sequence and a light chain variable region sequence of an anti-TTR antibody or antigen-binding fragment thereof as described herein. A Fab, Fab', F(ab')2, or scFv can be produced by any technique known to those of skill in the art. In certain aspects, the Fab, Fab', F(ab')$_2$, or scFv further comprises a moiety that extends the half-life of the antibody in vivo. The moiety is also termed a "half-life extending moiety." Any moiety known to those of skill in the art for extending the half-life of a Fab, Fab', F(ab')$_2$, or scFv in vivo can be used. For example, the half-life extending moiety can include a Fc region, a polymer, an albumin, or an albumin binding protein or compound. The polymer can include a natural or synthetic, optionally substituted straight or branched chain polyalkylene, polyalkenylene, polyoxylalkylene, polysaccharide, polyethylene glycol, polypropylene glycol, polyvinyl alcohol, methoxypolyethylene glycol, lactose, amylose, dextran, glycogen, or derivative thereof. Substituents can include one or more hydroxy, methyl, or methoxy groups. In certain aspects, the Fab, Fab', F(ab')$_2$, or scFv can be modified by the addition of one or more C-terminal amino acids for attachment of the half-life extending moiety. In certain aspects the half-life extending moiety is polyethylene glycol or human serum albumin. In certain aspects, the Fab, Fab', F(ab')$_2$, or scFv is fused to an Fc region.

An anti-TTR antibody or antigen-binding fragment thereof can be fused or conjugated (e.g., covalently or noncovalently linked) to a detectable label or substance. Examples of detectable labels or substances include enzyme labels, such as, glucose oxidase; radioisotopes, such as iodine ($^{125}I$, $^{121}I$) carbon ($^{14}C$), sulfur ($^{35}S$), tritium ($^{3}H$), indium ($^{121}$In), and technetium ($^{99}$Tc); luminescent labels, such as luminol; and fluorescent labels, such as fluorescein and rhodamine, and biotin. Such labeled antibodies or antigen-binding fragments thereof can be used to detect TTR (e.g., human TTR) protein.

III. Antibody Production

Antibodies and antigen-binding fragments thereof that immunospecifically bind to TTR (e.g., human TTR) can be produced by any method known in the art for the synthesis of antibodies and antigen-binding fragments thereof, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a certain aspect, provided herein is a method of making an antibody or antigen-binding fragment which immunospecifically binds to TTR (e.g., human TTR) comprising culturing a cell or host cell described herein. In a certain aspect, provided herein is a method of making an antibody or antigen-binding fragment thereof which immunospecifically binds to TTR (e.g., human TTR) comprising expressing (e.g., recombinantly expressing) the antibody or antigen-binding fragment thereof using a cell or host cell described herein (e.g., a cell or a host cell comprising polynucleotides encoding an antibody or antigen-binding fragment thereof described herein). In a particular aspect, the cell is an isolated cell. In a particular aspect, the exogenous polynucleotides have been introduced into the cell. In a particular aspect, the method further comprises the step of purifying the antibody or antigen-binding fragment obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies or antigen-binding fragments thereof can be prepared using a wide variety of techniques known in the art including the use of hybridoma, recombinant, and phage display technologies, yeast-based presentation technologies, or a combination thereof. For example, monoclonal antibodies or antigen-binding fragments thereof can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), or as described in Kohler G & Milstein C (1975) Nature 256: 495. Examples of yeast-based presentation methods that can be employed to select and generate the antibodies described herein include those disclosed in, for example, WO2009/036379A2; WO2010/105256; and WO2012/009568, each of which is herein incorporated by reference in its entirety.

In specific aspects, a monoclonal antibody or antigen-binding fragment thereof may be produced using the hybridoma method first described by Kohler et al., Nature, 256:495 (1975), as mentioned above. In the hybridoma method, a mouse or another appropriate host animal is immunized as above described to elicit lymphocytes that produce or are capable of producing antibodies that will specifically bind to the protein used for immunization, for example, variant mixtures of TTR. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986).

In specific aspects, a monoclonal antibody or antigen-binding fragment thereof is an antibody or antigen-binding fragment produced by a clonal cell (e.g., hybridoma or host cell producing a recombinant antibody or antigen-binding fragment), wherein the antibody or antigen-binding fragment immunospecifically binds to TTR (e.g., human TTR) as determined, e.g., by ELISA or other antigen-binding assays known in the art or in the Examples provided herein. In particular aspects, a monoclonal antibody or antigen-binding fragment thereof can be a rodent or murine antibody or antigen-binding fragment thereof. In particular aspects, a monoclonal antibody or antigen-binding fragment thereof can be a chimeric or a humanized antibody or antigen-binding fragment thereof. In certain aspects, a monoclonal antibody or antigen-binding fragment thereof can be a Fab fragment or an F(ab')$_2$ fragment. Monoclonal antibodies or antigen-binding fragments thereof described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies and antigen-binding fragments thereof expressed thereby are well known in the art (see, for example, Chapter 11 in: Short Protocols in Molecular Biology, (2002) 5th Ed., Ausubel F M et al., supra).

Antigen-binding fragments of antibodies described herein can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of a tetrameric antibody molecule and contains the complete light chain paired with the VH and CH1 domains of the heavy chain. An F(ab')$_2$ fragment contains the two antigen-binding arms of a tetrameric antibody molecule linked by disulfide bonds in the hinge region.

Further, the antibodies or antigen-binding fragments thereof described herein can also be generated using various phage display and/or yeast-based presentation methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antibody or antigen-binding fragment thereof that binds to a particular antigen can be selected or identified with antigen, e.g., using labeled antigen or antigen bound or captured to a solid surface or bead. Examples of phage display methods that can be used to make the antibodies or fragments described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

An antibody or antigen-binding fragment thereof can be selected from any class of immunoglobulins, including IgM, IgG, IgD, IgA, and IgE, and any isotype, including $IgG_1$, $IgG_2$, $IgG_3$ and $IgG_4$.

IIIa. Polynucleotides

In certain aspects, provided herein are polynucleotides comprising a nucleotide sequence encoding an antibody or antigen-binding fragment thereof described herein or a domain thereof (e.g., a variable light chain region and/or variable heavy chain region) that immunospecifically binds to a TTR (e.g., human TTR) antigen, and vectors, e.g., vectors comprising such polynucleotides for recombinant expression in host cells (e.g., *E. coli* and mammalian cells).

In particular aspects, provided herein are polynucleotides comprising nucleotide sequences encoding antibodies or antigen-binding fragments thereof, which immunospecifically bind to a TTR polypeptide (e.g., human TTR) and comprise an amino acid sequence as described herein, as well as antibodies or antigen-binding fragments that compete with such antibodies or antigen-binding fragments for binding to a TTR polypeptide (e.g., in a dose-dependent manner), or which bind to the same epitope as that of such antibodies or antigen-binding fragments.

Also provided herein is a polynucleotide comprising the same amino acid sequence as the VH of the antibody produced by the hybridoma of ATCC® deposit number PTA-125005. In some aspects, an antibody or antigen-binding fragment thereof comprising the polypeptide immunospecifically binds to TTR.

Also provided herein is a polynucleotide comprising the same amino acid sequence as the VL of the antibody produced by the hybridoma of ATCC® deposit number PTA-125005. In some aspects, an antibody or antigen-binding fragment thereof comprising the polypeptide immunospecifically binds to TTR.

Also provided herein is a polynucleotide comprising a nucleotide sequence encoding a polypeptide comprising a sequence selected from the group consisting of SEQ ID NOs:1-3 or comprising the amino acids of all of SEQ ID NOs:1-3. In some aspects, an antibody or antigen-binding fragment thereof comprising the polypeptide immunospecifically binds to TTR. Also provided herein is a polynucleotide comprising a nucleotide sequence encoding a polypeptide comprising a sequence selected from the group consisting of SEQ ID NOs:4-6 or comprising all of SEQ ID NOs:4-6. In some aspects, an antibody or antigen-binding fragment thereof comprising the polypeptide immunospecifically binds to TTR.

Also provided herein is a polynucleotide comprising a nucleotide sequence encoding a polypeptide comprising a sequence selected from the group consisting of SEQ ID NOs:8-10 or comprising the amino acids of all of SEQ ID NOs:8-10. In some aspects, an antibody or antigen-binding fragment thereof comprising the polypeptide immunospecifically binds to TTR. Also provided herein is a polynucleotide comprising a nucleotide sequence encoding a polypeptide comprising a sequence selected from the group consisting of SEQ ID NOs:11, 12, and 6 or comprising all of SEQ ID NOs:11, 12, and 6. In some aspects, an antibody or antigen-binding fragment thereof comprising the polypeptide immunospecifically binds to TTR.

Also provided herein is a polynucleotide comprising a nucleotide sequence encoding a heavy chain polypeptide comprising the same amino acid sequence as the heavy chain of the antibody produced by the hybridoma of ATCC® deposit number PTA-125005. In some aspects, an antibody or antigen-binding fragment thereof comprising the polypeptide immunospecifically binds to TTR.

Also provided herein is a polynucleotide comprising the same amino acid sequence as the light chain of the antibody produced by the hybridoma of ATCC® deposit number PTA-125005. In some aspects, an antibody or antigen-binding fragment thereof comprising the polypeptide immunospecifically binds to TTR.

A nucleic acid encoding a heavy chain variable domain or heavy chain and a nucleic acid encoding a light chain variable domain or light chain may be in the same polynucleotide or in different polynucleotides. A nucleic acid encoding a heavy chain variable domain or heavy chain and a nucleic acid encoding a light chain variable domain or light chain may be in the same vector or in different vectors.

Also provided herein is a composition comprising (i) a polynucleotide comprising a nucleic acid encoding a heavy chain variable domain, wherein the nucleic acid encoding the heavy chain variable domain comprises the heavy chain variable domain-encoding sequence in the hybridoma of ATCC® deposit number PTA-125005, and (ii) a polynucleotide comprising a nucleic acid encoding a light chain variable domain, wherein the nucleic acid encoding the light chain variable domain comprises the light chain variable domain-encoding sequence in the hybridoma of ATCC® deposit number PTA-125005. The nucleic acid encoding the heavy chain variable domain and the nucleic acid encoding the light chain variable domain may be in the same polynucleotide or in different polynucleotides. The nucleic acid encoding the heavy chain variable domain and the nucleic acid encoding the light chain variable domain may be in the same vector or in different vectors.

Also provided herein are polynucleotides comprising a nucleotide sequence that encodes SEQ ID NOs:1-3 and/or 4-6. Also provided herein are polynucleotides comprising a nucleotide sequence that encodes SEQ ID NOs:8-10 and/or 11, 12, and 6.

Also provided herein are polynucleotides that are at least about 80%, 85%, or 90% identical to a nucleotide sequence that encodes SEQ ID NOs:1-3 and/or 4-6. Also provided herein are polynucleotides that are at least about 80%, 85%, or 90% identical to a nucleotide sequence that encodes SEQ ID NOs:8-10 and/or 11, 12, and 6.

Also provided herein are polynucleotides comprising a nucleotide sequence that is at least about 95% identical to a nucleotide sequence that encodes SEQ ID NOs:1-3 and/or 4-6. Also provided herein are polynucleotides comprising a nucleotide sequence that is at least about 96% identical to a nucleotide sequence that encodes SEQ ID NOs:1-3 and/or 4-6. Also provided herein are polynucleotides comprising a nucleotide sequence that is at least about 97% identical to a nucleotide sequence that encodes SEQ ID NOs:1-3 and/or 4-6. Also provided herein are polynucleotides comprising a nucleotide sequence that is at least about 98% identical to a nucleotide sequence that encodes SEQ ID NOs:1-3 and/or 4-6. Also provided herein are polynucleotides comprising a nucleotide sequence that is at least about 99% identical to a nucleotide sequence that encodes SEQ ID NOs:1-3 and/or 4-6.

Also provided herein are polynucleotides comprising a nucleotide sequence that is at least about 95% identical to a nucleotide sequence that encodes SEQ ID NOs:8-10 and/or 11, 12, and 6. Also provided herein are polynucleotides comprising a nucleotide sequence that is at least about 96% identical to a nucleotide sequence that encodes SEQ ID NOs: 8-10 and/or 11, 12, and 6. Also provided herein are polynucleotides comprising a nucleotide sequence that is at least about 97% identical to a nucleotide sequence that encodes SEQ ID NOs: 8-10 and/or 11, 12, and 6. Also provided herein are polynucleotides comprising a nucleotide sequence that is at least about 98% identical to a nucleotide sequence that encodes SEQ ID NOs: 8-10 and/or 11, 12, and 6. Also provided herein are polynucleotides comprising a nucleotide sequence that is at least about 99% identical to a nucleotide sequence that encodes SEQ ID NOs: 8-10 and/or 11, 12, and 6.

In a particular aspect, a polynucleotide or combination of polynucleotides provided herein comprises a nucleotide sequence or combination of nucleotide sequences encoding an antibody or antigen-binding fragment thereof that immunospecifically binds to TTR (e.g., human TTR), wherein the antibody or antigen-binding fragment thereof comprises a heavy chain, wherein the heavy chain comprises the same amino acid sequence as the VH of the antibody produced by the hybridoma of ATCC® deposit number PTA-125005, and a constant region comprising the amino acid sequence of a human gamma (γ) heavy chain constant region (e.g., IgG$_1$).

In a particular aspect, a polynucleotide or combination of polynucleotides provided herein comprises a nucleotide sequence or combination of nucleotide sequences encoding an antibody or antigen-binding fragment thereof that immunospecifically binds to TTR (e.g., human TTR), wherein the antibody or antigen-binding fragment thereof comprises a light chain, wherein the light chain comprises the same amino acid sequence as the VL of the antibody produced by the hybridoma of ATCC® deposit number PTA-125005, and a constant region comprising the amino acid sequence of a human kappa light chain constant region.

Also provided herein are polynucleotides encoding an anti-TTR antibody or antigen-binding fragment thereof described herein or a domain thereof that are optimized, e.g., by codon/RNA optimization, replacement with heterologous signal sequences, and elimination of mRNA instability elements. Methods to generate optimized nucleic acids encoding an anti-TTR antibody or antigen-binding fragment thereof or a domain thereof (e.g., heavy chain, light chain, VH domain, or VL domain) for recombinant expression by introducing codon changes (e.g., a codon change that encodes the same amino acid due to the degeneracy of the genetic code) and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly.

A polynucleotide encoding an antibody or antigen-binding fragment thereof described herein or a domain thereof can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody or antigen-binding fragment thereof. Such PCR amplification methods can be used to obtain nucleic acids comprising the sequence encoding the variable light chain region and/or the variable heavy chain region of an antibody or antigen-binding fragment thereof. The amplified nucleic acids can be cloned into vectors for expression in host cells and for further cloning, for example, to generate chimeric and humanized antibodies or antigen-binding fragments thereof.

Polynucleotides provided herein can be, e.g., in the form of RNA or in the form of DNA. DNA includes cDNA, genomic DNA, and synthetic DNA, and DNA can be double-stranded or single-stranded. If single stranded, DNA can be the coding strand or non-coding (anti-sense) strand. In certain aspects, the polynucleotide is a cDNA or a DNA lacking one more endogenous introns. In certain aspects, a polynucleotide is a non-naturally occurring polynucleotide. In certain aspects, a polynucleotide is recombinantly produced. In certain aspects, the polynucleotides are isolated. In certain aspects, the polynucleotides are substantially pure. In certain aspects, a polynucleotide is purified from natural components.

IIIb. Cells and Vectors

In certain aspects, provided herein are vectors (e.g., expression vectors) comprising polynucleotides comprising nucleotide sequences encoding anti-TTR antibodies and antigen-binding fragments thereof or a domain thereof for recombinant expression in host cells, preferably in mammalian cells. Also provided herein are cells, e.g., host cells, comprising such vectors for recombinantly expressing anti-TTR antibodies or antigen-binding fragments thereof described herein. In a particular aspect, provided herein are methods for producing an antibody or antigen-binding fragments thereof described herein, comprising expressing such antibody or antigen-binding fragment thereof in a host cell.

In certain aspects, recombinant expression of an antibody or antigen-binding fragment thereof or domain thereof described herein (e.g., a heavy or light chain described herein) that specifically binds to TTR (e.g., human TTR) involves construction of an expression vector containing a polynucleotide that encodes the antibody or antigen-binding fragment thereof or domain thereof. Once a polynucleotide encoding an antibody or antigen-binding fragment thereof or domain thereof (e.g., heavy or light chain variable domain) described herein has been obtained, the vector for the production of the antibody or antigen-binding fragment thereof can be produced by recombinant DNA technology using techniques well known in the art. Thus, methods for preparing a protein by expressing a polynucleotide containing an antibody or antigen-binding fragment thereof or domain thereof (e.g., light chain or heavy chain) encoding nucleotide sequence are described herein. Methods which are well known to those skilled in the art can be used to construct expression vectors containing antibody or antigen-binding fragment thereof or domain thereof (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody or antigen-binding fragment thereof described herein, a heavy or light chain, a heavy or light chain variable domain, or a heavy or light chain CDR, operably linked to a promoter. Such vectors can, for example, include the nucleotide sequence encoding the constant region of the antibody or antigen-binding fragment thereof (see, e.g., International Publication Nos. WO 86/05807 and WO 89/01036; and U.S. Pat. No. 5,122,464), and variable domains of the antibody or antigen-binding fragment thereof can be cloned into such a vector for expression of the entire heavy, the entire light chain, or both the entire heavy and light chains.

An expression vector can be transferred to a cell (e.g., host cell) by conventional techniques, and the resulting cells can then be cultured by conventional techniques to produce an antibody or antigen-binding fragment thereof described herein, e.g., an antibody or antigen-binding fragment thereof comprising the six CDRs of SEQ ID NOs:1-6, the six CDRS of SEQ ID NOs:8-12 and 6, the same amino acid sequence as the VH of the antibody produced by the hybridoma of ATCC® deposit number PTA-125005, the same amino acid sequence as the VL of the antibody produced by the hybridoma of ATCC® deposit number PTA-125005, the same amino acid sequence as the VH of the antibody produced by the hybridoma of ATCC® deposit number PTA-125005, and the same amino acid sequence as the VL of the antibody produced by the hybridoma of ATCC® deposit number PTA-125005, the same amino acid sequence as the heavy chain of the antibody produced by the hybridoma of ATCC® deposit number PTA-125005, the same amino acid sequence as the light chain of the antibody produced by the hybridoma of ATCC® deposit number PTA-125005, or the same amino acid sequence as the heavy chain of the antibody produced by the hybridoma of ATCC® deposit number PTA-125005, and the same amino acid sequence as the light chain of the antibody produced by the hybridoma of ATCC® deposit number PTA-125005. Thus, provided herein are host cells containing a polynucleotide encoding an antibody or antigen-binding fragment thereof described herein, e.g., an antibody or antigen-binding fragment thereof comprising the six CDRs of SEQ ID NOs:1-6, the six CDRs of SEQ ID NOs:8-12 and 6, the same amino acid sequence as the VH of the antibody produced by the hybridoma of ATCC® deposit number PTA-125005, the same amino acid sequence as the VL of the antibody produced by the hybridoma of ATCC® deposit number PTA-125005, the same amino acid sequence as the VH of the antibody produced by the hybridoma of ATCC® deposit number PTA-125005, and the same amino acid sequence as the VL of the antibody produced by the hybridoma of ATCC® deposit number PTA-125005, the same amino acid sequence as the heavy chain of the antibody produced by the hybridoma of ATCC® deposit number PTA-125005, the same amino acid sequence as the light chain of the antibody produced by the hybridoma of ATCC® deposit number PTA-125005, or the same amino acid sequence as the heavy chain of the antibody produced by the hybridoma of ATCC® deposit number PTA-125005 and the same amino acid sequence as the light chain of the antibody produced by the hybridoma of ATCC® deposit number PTA-125005, operably linked to a promoter for expression of such sequences in the host cell. In certain aspects, for the expression of double-chained antibodies or antigen-binding fragments thereof, vectors encoding both the heavy and light chains, individually, can be co-expressed in the host cell for expression of the entire immunoglobulin, as detailed below. In certain aspects, a host cell contains a vector comprising a polynucleotide encoding both the heavy chain and light chain of an antibody described herein or a domain thereof. In specific aspects, a host cell contains two different vectors, a first vector comprising a polynucleotide encoding a heavy chain or a heavy chain variable region of an antibody or antigen-binding fragment thereof described herein, and a second vector comprising a polynucleotide encoding a light chain or a light chain variable region of an antibody described herein (e.g., an antibody comprising the six CDRs of SEQ ID NOs:1-6 or the six CDRs of SEQ ID NOs:8-12 and 6), or a domain thereof. In other aspects, a first host cell comprises a first vector comprising a polynucleotide encoding a heavy chain or a heavy chain variable region of an antibody or antigen-binding fragment thereof described herein, and a second host cell comprises a second vector comprising a polynucleotide encoding a light chain or a light chain variable region of an antibody or antigen-binding fragment thereof described herein (e.g., an antibody or antigen-binding fragment thereof comprising the six CDRs of SEQ ID NOs:1-6 or the six CDRS of SEQ ID NOs:8-12 and 6). In specific aspects, a heavy chain/heavy chain variable region expressed by a first cell associated with a light chain/light chain variable region of a second cell to form an anti-TTR antibody or antigen-binding fragment thereof described herein (e.g., antibody or antigen-binding fragment thereof comprising the six CDRs of SEQ ID NOs:1-6 or the six CDRS of SEQ ID NOs:8-12 and 6). In certain aspects, provided herein is a population of host cells comprising such first host cell and such second host cell.

In a particular aspect, provided herein is a population of vectors comprising a first vector comprising a polynucleotide encoding a light chain/light chain variable region of an anti-TTR antibody or antigen-binding fragment thereof described herein, and a second vector comprising a polynucleotide encoding a heavy chain/heavy chain variable region of an anti-TTR antibody or antigen-binding fragment thereof described herein (e.g., antibody or antigen-binding fragment thereof comprising the CDRs of SEQ ID NOs:1-6 or the CDRS of SEQ ID NOs:8-12 and 6). Alternatively, a single vector can be used which encodes, and is capable of expressing, both heavy and light chain polypeptides.

A variety of host-expression vector systems can be utilized to express antibodies and antigen-binding fragments thereof described herein (e.g., an antibody or antigen-binding fragment thereof comprising the CDRs of SEQ ID NOs:1-6 or the CDRS of SEQ ID NOs:8-12 and 6) (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody or antigen-binding fragment thereof described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO (e.g., CHO-K1 SP), BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific aspect, cells for expressing antibodies and antigen-binding fragments thereof described herein (e.g., an antibody or antigen-binding fragment thereof comprising the CDRs of SEQ ID NOs:1-6 or the CDRS of SEQ ID NOs:8-12 and 6) are CHO cells, for example CHO cells from the CHO GS System™ (Lonza) or CHO-K1 SP cells. In a particular aspect, cells for expressing antibodies described herein are human cells, e.g., human cell lines. In a specific aspect, a mammalian expression vector is pOptiVEC™ or pcDNA3.3. In a particular aspect, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In certain aspects, antibodies or antigen-binding fragments thereof described herein are produced by CHO cells or NS0 cells.

In addition, a host cell strain can be chosen which modulates the expression of the inserted sequences, or modifies and processes the gene product in the specific fashion desired. Such modifications (e.g., glycosylation) and processing (e.g., cleavage) of protein products can contribute to the function of the protein. To this end, eukaryotic host cells that possess the cellular machinery for proper processing of the primary transcript, glycosylation, and phosphorylation of the gene product can be used. Such mammalian host cells include but are not limited to CHO, VERO, BHK, HeLa, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain aspects, anti-TTR antibodies described herein (e.g., an antibody or antigen-binding fragment thereof comprising the CDRs of SEQ ID NOs:1-6 or the CDRS of SEQ ID NOs:8-12 and 6) are produced in mammalian cells, such as CHO cells, e.g., CHO-K1 or CHO-K1 SP cells. In certain aspects, anti-TTR antibodies described herein (e.g., an anti-body or antigen-binding fragment thereof comprising the CDRs of SEQ ID NOs:1-6 or the CDRS of SEQ ID NOs:8-12 and 6) are produced in mammalian cells, such as HEK-293 cells, e.g., 293F cells.

In some aspects, a signal peptide is used in constructing a vector containing the VH and/or VL or the heavy and/or light chain of an antibody or antigen-binding fragment thereof provided herein.

Once an antibody or antigen-binding fragment thereof described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or antigen-binding fragments thereof described herein can be fused to heterologous polypeptide sequences described herein or otherwise known in the art to facilitate purification.

In specific aspects, an antibody or antigen-binding fragment thereof described herein is isolated or purified. Generally, an isolated antibody or antigen-binding fragment thereof is one that is substantially free of other antibodies or antigen-binding fragments thereof with different antigenic specificities than the isolated antibody or antigen-binding fragment thereof. For example, in a particular aspect, a preparation of an antibody or antigen-binding fragment thereof described herein is substantially free of cellular material and/or chemical precursors.

IV. Pharmaceutical Compositions Comprising Anti-TTR Antibodies and Antigen-Binding Fragments Thereof Provided herein are compositions comprising an antibody or antigen-binding fragment thereof described herein having the desired degree of purity in a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed.

In various aspects, compositions comprising an anti-TTR antibody or antigen-binding fragment thereof are provided in formulations with a pharmaceutically acceptable carrier (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)).

Pharmaceutical compositions described herein can be useful in decreasing the toxicity of TTR fibrils (e.g., on human cardiomyocytes) and/or inhibiting accumulation of TTR aggregates (e.g., in an organ such as a heart and/or kidney). Pharmaceutical compositions described herein can be useful in treating a condition such as a TTR amyloidosis.

The pharmaceutical compositions described herein are in one aspect for use as a medicament. The pharmaceutical compositions described herein are in one aspect for use as a diagnostic, e.g., to detect the presence of TTR in a sample obtained from a patient (e.g., a human patient).

The compositions to be used for in vivo administration can be sterile. This is readily accomplished by filtration through, e.g., sterile filtration membranes.

In some aspects, pharmaceutical compositions are provided, wherein the pharmaceutical composition comprises anti-TTR antibodies or antigen-binding fragments thereof described herein and a pharmaceutically acceptable carrier.

In some aspects, a pharmaceutical composition comprises (i) an isolated antibody or antigen-binding fragment thereof that specifically binds to human TTR, comprising (a) the complementarity determining region (CDR) H1, CDR H2, CDR H3 and CDR L1, CDR L2, and CDR L3 sequences of SEQ ID NOs:1-6, respectively, (b) the CDR H1, CDR H2, CDR H3 and CDR L1, CDR L2, and CDR L3 sequences of SEQ ID NOs:8-12 and 6, respectively, (c) the same amino acid sequence as the VH of the antibody produced by the hybridoma of ATCC® deposit number PTA-125005, and the same amino acid sequence as the VL of the antibody produced by the hybridoma of ATCC® deposit number PTA-125005, or (d) the same amino acid sequence as the heavy chain of the antibody produced by the hybridoma of ATCC® deposit number PTA-125005, and the same amino acid sequence as the light chain of the antibody produced by the hybridoma of ATCC® deposit number PTA-125005, and (ii) a pharmaceutically acceptable excipient.

V. Methods of Using Anti-TTR Antibodies and Antigen-Binding Fragments Thereof

Va. Therapeutic and Prophylactic Uses and Methods

In one aspect, presented herein are methods for treating or preventing a TTR amyloidosis in a subject, comprising administering to a subject in need thereof an anti-TTR antibody or antigen-binding fragment thereof described herein, or a pharmaceutical composition thereof as described above and herein.

In another aspect, an anti-TTR antibody or antigen-binding fragment thereof, or pharmaceutical composition, is administered to a patient (e.g., a human patient) to decrease the toxicity of TTR fibrils (e.g., on human cardiomyocytes). In another aspect, an anti-TTR antibody or antigen-binding fragment thereof, or pharmaceutical composition, is administered to a patient (e.g., a human patient) to inhibit accumulation of TTR aggregates (e.g., in an organ such as a heart and/or kidney).

Usually, the patient is a human, but non-human mammals including transgenic mammals can also be treated.

In some aspects, the present invention relates to an antibody or antigen-binding fragment thereof or pharmaceutical composition provided herein for use as a medicament. In some aspects, the present invention relates to an antibody or antigen-binding fragment thereof or pharmaceutical composition provided herein, for use in a method for the treatment or prevention of a TTR amyloidosis. In some aspects, the present invention relates to an antibody or antigen-binding fragment thereof or pharmaceutical composition provided herein, for use in a method for the treatment or prevention of a TTR amyloidosis in a subject, comprising administering to the subject an effective amount of an antibody or antigen-binding fragment thereof or pharmaceutical composition provided herein.

An antibody or antigen-binding fragment thereof or composition described herein can be delivered to a subject by a variety of routes, such as parenteral, subcutaneous, intravenous, intradermal, transdermal, and intranasal. In one aspect, the antibody or antigen-binding fragment thereof or composition is administered by an intravenous route.

The amount of an antibody or antigen-binding fragment thereof or composition which will be effective in the treatment or prevention of a condition will depend on the nature of the disease. The precise dose to be employed in a composition will also depend on the route of administration, and the seriousness of the disease.

Vb. Detection and Diagnostic Uses

An anti-TTR antibody or antigen-binding fragment thereof described herein can be used to assay TTR protein levels in a biological sample using classical methods known to those of skill in the art, including immunoassays, such as the enzyme linked immunosorbent assay (ELISA), fluorescence-activated cell sorting (FACS), immunohistochemistry (IHC), immunoprecipitation, and Western blotting. Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody or antigen-binding fragment thereof described herein. Alternatively, a second antibody or antigen-binding fragment thereof that recognizes an anti-TTR antibody or antigen-binding fragment thereof described herein can be labeled and used in combination with an anti-TTR antibody or antigen-binding fragment thereof to detect TTR protein levels.

Assaying for the expression level of TTR protein is intended to include qualitatively or quantitatively measuring or estimating the level of a TTR protein in a first biological sample either directly (e.g., by determining or estimating absolute protein level) or relatively (e.g., by comparing to the disease associated protein level in a second biological sample). TTR polypeptide expression level in the first biological sample can be measured or estimated and compared to a standard TTR protein level, the standard being taken from a second biological sample obtained from an individual not having the disorder or being determined by averaging levels from a population of individuals not having the disorder. As will be appreciated in the art, once the "standard" TTR polypeptide level is known, it can be used repeatedly as a standard for comparison.

As used herein, the term "biological sample" refers to any biological sample obtained from a subject, cell line, tissue, or other source of cells potentially expressing TTR. Methods for obtaining tissue biopsies and body fluids from animals (e.g., humans) are well known in the art. A biological sample may also be a blood sample.

An anti-TTR antibody or antigen-binding fragment thereof described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of TTR presence may be utilized to predict, diagnose and monitor to evaluate patient samples including those known to have or suspected of having a TTR amyloidosis. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

Anti-TTR antibodies and antigen-binding fragments thereof described herein can carry a detectable or functional label.

Examples of detectable moieties that can be used herein include but are not limited to radioactive isotopes, phosphorescent chemicals, chemiluminescent chemicals, fluorescent chemicals, enzymes, fluorescent polypeptides, and epitope tags. The detectable moiety can be a member of a binding pair, which is identifiable via its interaction with an additional member of the binding pair, and a label which is directly visualized.

When fluorescence labels are used, currently available microscopy and fluorescence-activated cell sorter analysis (FACS) or combination of both methods procedures known in the art may be utilized to identify and to quantitate the specific binding members. Anti-TTR antibodies or antigen-binding fragments thereof described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-TTR antibody can carry a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$CU, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-TTR antibody or antigen-binding fragment to TTR (e.g., human TTR). In the instance where the label is an enzyme, detection may be accomplished by any of the presently utilized colorimetric, spectrophotometric, fluorospectrophotometric, amperometric, or gasometric techniques as known in the art. This can be achieved by contacting a sample or a control sample with an anti-TTR antibody or antigen-binding fragment thereof under conditions that allow for the formation of a complex between the antibody or antigen-binding fragment thereof and TTR. Any complexes formed between the antibody or antigen-binding fragment thereof and TTR are detected and compared in the sample and the control. The antibodies or antigen-binding fragments thereof described herein can also be used to purify TTR via immunoaffinity purification (see e.g., Example 3).

Also included herein is an assay system which may be prepared in the form of a test kit for the quantitative analysis of the extent of the presence of, for instance, TTR. The system or test kit may comprise a labeled component, e.g., a labeled antibody or antigen-binding fragment, and one or more additional immunochemical reagents. See, e.g., Section VI below for more on kits.

In some aspects, methods for in vitro detecting TTR in a sample, comprising contacting said sample with an antibody or antigen-binding fragment thereof, are provided herein. In some aspects, provided herein is the use of an antibody or antigen-binding fragment thereof provided herein, for in vitro detecting TTR in a sample. In one aspect, provided herein is an antibody or antigen-binding fragment thereof or pharmaceutical composition provided herein for use in the detection of TTR in a subject or a sample obtained from a subject. In one aspect, provided herein is an antibody or antigen-binding fragment thereof or pharmaceutical composition provided herein for use as a diagnostic. In one aspect, the antibody comprises a detectable label. In one aspect, TTR is human TTR. In one aspect, the subject is a human.

VI. Kits

Provided herein are kits comprising one or more antibodies or antigen-binding fragments thereof described herein or conjugates (e.g., detection conjugates) thereof. As provided herein, kits can be used in diagnostic methods. In one aspect, a kit comprises an antibody or antigen-binding fragment thereof described herein, preferably a purified antibody or antigen-binding fragment thereof, in one or more containers.

In a specific aspect, kits described herein contain a substantially isolated TTR antigen (e.g., human TTR) that can be used as a control. In specific aspects, a kit provided herein can include a recombinantly produced or chemically synthesized TTR antigen. The TTR antigen provided in the kit can also be attached to a solid support.

In another specific aspect, the kits described herein further comprise a control antibody or antigen-binding fragment thereof which does not react with a TTR antigen. In another specific aspect, kits described herein contain one or more elements for detecting the binding of an antibody or antigen-binding fragment thereof to a TTR antigen (e.g., the antibody or antigen-binding fragment thereof can be conjugated to a detectable substrate such as a fluorescent compound, an enzyme, an enzymatic substrate, a radioactive compound, or a luminescent compound, or a second antibody or antigen-binding fragment thereof, which recognizes the first antibody or antigen-binding fragment thereof, can be conjugated to a detectable substrate). In a more specific aspect, the detecting means of the above described kit includes a solid support to which a TTR antigen is attached. Such a kit can also include a non-attached reporter-labeled anti-mouse/rodent antibody or antigen-binding fragment thereof. In this aspect, binding of the antibody or antigen-binding fragment thereof to the TTR antigen can be detected by binding of the said reporter-labeled antibody or antigen-binding fragment thereof.

In another specific aspect, the kits described herein further comprise a therapeutic anti-TTR antibody or antigen-binding fragment thereof and/or information that a therapeutic anti-TTR antibody or antigen-binding fragment thereof should be administered when TTR is detected in a sample using an anti-TTR antibody or antigen-binding fragment thereof provided herein.

VII. Examples

The examples in this section (i.e., Section VII) are offered by way of illustration and not by way of limitation.

Materials and Methods

Preparation of Fibrillar TTR

Lyophilized purified TTR monomer (1 mg Alexotech, Sweden) was thawed at room temperature for 10 minutes followed by addition of 0.5 ml of sterile PBS to a final concentration of 2 mg/ml. TTR was transferred to a new low-binding, sterile 1.5 ml microcentrifuge tube (Protein LoBind Tube 1.5, Eppendorf tubes, Cat no.: 022431081) followed by addition of 500 µl TTR aggregation buffer×2 (20 mM sodium acetate (pH 4.3), 200 mM KCl, and 20 mM EDTA) to generate fibrillar TTR in a final volume of 1 ml and at a final concentration of 1 mg/ml. The tube was placed in a 37° C. incubation for 72 hours (maximum 4 days). The solution was divided into aliquots (20-30 µl) into sterile microcentrifuge tubes and stored at −80° C. before use.

Cell Viability Assays

The toxicity of TTR fibrils was assessed by the 3-(4,5-dimethylthiazol-2-yl)-2,5-diphenyltetrazolium bromide MTT cell viability assay on differentiated rat cardiomyocytes H9c2 cells. For the MTT assay, cells were plated at a density of 1,600 cells per well on 96-well plates in 100 µl of culture medium per well. Following 72 hours, the medium was exchanged with 100 µl of fresh medium containing 1% FBS and 10 µM of retanoic acid (RA) for cardiac cell differentiation. After 7 additional days, 2.5 µM of TTR fibrils were incubated with CGX304 or sham 1G4-2 for an additional 4 hours at room temperature and added to the differentiated cardiomyocytes cells for 24 hours at 37° C. Control samples were prepared with the addition of identical volumes of buffer. After 24 hours of incubation, the cells were incubated for another 4 hours with 100 µl of serum-free Dulbecco's modified Eagle's medium without phenol red, containing 0.5 mg/ml MTT. Then, 100 µl of cell lysis solution (20% SDS, 50% N,N-dimethylformamide) was added to each well, and the samples were incubated overnight at 37° C. to allow complete lysis. The absorbance of the formazan was measured at 570 nm in a Tecan infinite 200 pro microplate reader (Tecan, Männedorf, Switzerland).

Uptake of TTR Fibrils in Mouse Microglia Cells

BV-2 (mouse microglia, ICLC ATL03001) cells were split into 12-well culture plates (Greiner CELLSTAR multiwell culture plates) on the day before the experiment. 0.3 µM TTR fibrils conjugated with Alexa 488, pre-incubated with 0.05, 0.1 0.2, 0.5, 1, 2, 3, or 4 µg/ml CGX304 or 0.1, 1, 3, 4 or µg/ml 1G4-2 (sham) for 2 hours at room temperature, were added to cells with culture media (RPMI 1640, 10% FBS, 2 mM L-Glutamine, 1% Pen/Strep). The conditioned medium was also pre-incubated with CGX304 (without fibrillar TTR) for 2 hours as a control. Cells were then incubated at 37° C. for 24 hours and harvested. Extracellular and cell surface aggregated TTR conjugated with Alexa 488 in cell pellet was quenched by incubation of 0.4% trypan blue in PBS (pH 4.4) for 1 minute. Flow cytometry (FL1—blue laser (488 nm) was used to measure TTR fibrils (conjugated to ALEXA fluor 488) uptake indicated as relative geomean fluorescence intensity (gMFI). Cytochalasin D (Cyto D) is an antibiotic which is used to inhibit cellular uptake (control).

Uptake of TTR Fibrils in Human Monocytes

THP-1 (human monocytes, ATCC® TIB-202) cells were split into 12-well culture plates (Greiner CELLSTAR multiwell culture plates) on the day before the experiment. 0.3 µM TTR fibrils conjugated with Alexa 488, pre-incubated with either 0.1, or 1 µg/ml CGX304 or 0.1 or 1 µg/ml 1G4-2 (sham) for 2 hours at room temperature, were added to cells with culture media (RPMI 1640, 10% FBS, 2 mM L-Glutamine, 1% Pen/Strep). The conditioned medium was also pre-incubated with CGX304 (without fibrillar TTR) for 2 hours as a control. Cells were then incubated at 37° C. for 1.5 hours and harvested. Extracellular and cell surface aggregated TTR conjugated with Alexa 488 in cell pellet was quenched by incubation of 0.4% trypan blue in PBS (pH 4.4) for 1 minute. Flow cytometry (FL1—blue laser (488 nm)) was used to measure TTR fibrils (conjugated to ALEXA fluor 488) uptake indicated as relative geomean fluorescence intensity (gMFI). Cytochalasin D (Cyto D) is an antibiotic which is used to inhibit cellular uptake (control).

Fibrillar TTR Protein Levels Post Cell Uptake of Human Monocytes U937

U937 (human monocytes, ATCC® CRL-1593.2) cells were split into 24-well culture plates (Greiner CELLSTAR multiwell culture plates) on the day before the experiment. 0.2 µM TTR fibrils pre-incubated with 0.5 µg/ml CGX304, Ab-D, or 1G4-2 (sham) for 30 minutes at room temperature, were added to cells with culture media (RPMI 1640, 10% FBS, 2 mM L-Glutamine, 1% Pen/Strep, 10% HEPES and 0.05 mM of 2-mercaptoethanol). The conditioned medium was also pre-incubated with CGX304 (without fibrillar TTR) for 30 minutes as a control. Cells were then incubated at 37° C. for 0 and 60 minutes and harvested. Harvested cells were washed ×2 with PBS and resuspended in lysis buffer for detecting TTR protein levels using western blot. 20 µg of U937 lysates were loaded on a SDS-PAGE (10% acrylamide) and transferred to protran nitrocellulose membranes. Membranes were analyzed by immunoblot for transthyretin using mouse anti-human TTR (mouse IgG1 anti-human transthyretin 39-44, Alexotech; 1:1000) followed by peroxidase-AffiniPure goat anti-mouse IgG (Jackson; 1:10,000) before enhanced chemiluminescence development. Image Lab software (bio-rad) was used to calculate the volume intensity (pixels) normalized to GAPDH for TTR uptake quantification.

Immunopercipitation of Serum-Derived Transthyretin by CGX304

Human sera obtained from TTR amyloidosis patients were immunoprecipitated with different amounts of CGX304 (5, 10, and 50 µg) bound to Dynabeads protein A (Dynabeads® Protein A for IP 1 ml, Life technologies, Grand Island, NY, USA) following manufacturer's instructions, then separated by SDS-PAGE (Bis-Tris 10% acrylamide) and transferred to protran nitrocellulose membranes. Membranes were analyzed by immunoblot for transthyretin using mouse anti-human TTR (mouse IgG1 anti-human transthyretin 39-44, Alexotech; 1:1000) following peroxidase-AffiniPure goat anti-mouse IgG (Jackson; 1:10,000) before enhanced chemiluminescence development. 100 ng of recombinant human wild-type TTR and PBS were immunoprecipitated with 50 µg of CGX304 bound to Dynabeads as positive and negative control respectively.

Animals

WT rats (Sprague-Dawley) were purchased from Envigo RMS (Israel), Ltd. All housing, breeding, and procedures were performed according to the National Institute of Health (NIH) Guide for the Care and Use of Experimental Animals and approved by the Kaplan Medical Center Institutional Animal Care and Use Committee.

CGX304 Clears Aggregated TTR Detected by PYP Tech Scan Combined with Computer Tomography Scanning (CT) in the Heart of Rodents 14 male (3 groups) Sprague-Dawley rats (200 grams) were anesthetized by Isoflurane before their chests were opened for TTR fibril injection to the heart. Matrigel was added to the fibrillar TTR (30 µg in PBS; 50 µl volume) in a 1:1 volume ratio and loaded (100 µl) to a 1 ml syringe using a 27G needle and kept on ice until rat was ready for injection. Control animals received sterile PBS and Matrigel (1:1) with no TTR. A single needle insertion into the apex of the rat's heart was used to spread the fibrillar TTR for Technetium pyrophosphate ($^{99m}$Tc-PYP) scintigraphy detection assay model. 4 mCi of $^{99m}$Tc-PYP was administered intravenously (IV) immediately after surgery. 30 minutes before surgery, animals received (IP) CGX304 (5 mg/kg), 1G4-2 (sham), or matrigel only (negative control) treatment. 1 hour from surgery, animals underwent serial $^{99m}$Tc-PYP planar cardiac imaging and CT-PET scanning for transthyretin detection. Cardiac retention was assessed quantitatively (region of interest drawn over the heart, copied, and mirrored over the contralateral chest wall) to calculate a heart-to-contralateral chest wall (Cardiac/Chest wall) ratio. For biochemical studies, the heart was removed, tissues were homogenized for protein purification and CGX304 (mouse IgG1) protein levels were detected using a calibrated ELISA assay for mouse IgG1 (IgG1 Mouse ELISA Kit; ThermoFisher Scientific—cat #88-50410-22).

CGX304 Clears Aggregated TTR Detected by PYP Tech Scan Combined with Computer Tomography Scanning (CT) in Rodent Kidneys 3 Male Sprague-Dawley rats (200 grams) were anesthetized by Isoflurane before surgery of TTR fibril injection to the kidneys. Aggregated TTR (10 µg) was mixed together with CGX304 or sham treatment before matrigel was added in a 1:1 volume ratio and loaded to a 10 µl syringe using a 33G needle and kept on ice until rat was ready for injection. Right kidney received sterile sham treatment, while left kidney received CGX304 treatment. A single needle insertion into the left (CGX304) and right (sham) kidneys of rats was used to spread the fibrillar TTR-treatment mix for Technetium pyrophosphate ($^{99m}$Tc-PYP) scintigraphy detection assay model. 2 mCi of $^{99m}$Tc-PYP was administered IV immediately after surgery. 1 hour from surgery, animals underwent serial $^{99m}$Tc-PYP planar cardiac imaging and CT-PET scanning for transthyretin detection. Kidney retention was assessed quantitatively to calculate a right-to-left kidney (Right/Left kidney) ratio. For biochemical studies, kidneys were removed and tissues were immediately frozen and stored at −80° C. until used.

Western Blot for Detection of Aggregated TTR in Rodent Kidneys

12 µg of left/right kidney protein lysate were loaded on a SDS-PAGE (10% acrylamide) and transferred to protran nitrocellulose membranes. Membranes were analyzed by immunoblot for transthyretin using rabbit anti-human TTR (mouse IgG1 anti human transthyretin 39-44, Alexotech; 1:1000) followed by peroxidase-AffiniPure goat anti-rabbit IgG (Jackson; 1:10,000) before enhanced chemiluminescence development.

CGX304 Pharmacokinetics/Pharmacodynamics—Antibody Clearance/Rat Prealbumin Levels in Serum Rats were divided into 3 groups of n=3 to characterize the plasma concentration-endogenous TTR effect relationship for CGX304 in a pharmacokinetics/pharmacodynamics model. Each group received a different initial concentration of CGX304 (0.5 mg/kg, 2.5 mg/kg, or 10 mg/kg) IV. Blood samples were collected 1 hour, 2 hours, 72 hours, 7 days, and 28 days post CGX304 IV injection. For biochemical studies, the heart was removed 28 days post IV injections, and tissues were homogenized for protein purification. CGX304 (mouse IgG1) protein levels (PK) in blood serum and heart tissue total protein content lysate were detected using a calibrated ELISA assay for mouse IgG1 (IgG1 Mouse ELISA Kit; ThermoFisher Scientific—cat #88-50410-22), while free endogenous rat pre-albumin (TTR) levels were detected using a calibrated ELISA assay for rat TTR (Rat TTR/Transthyretin ELISA Kit (Sandwich ELISA)—LS-F9963).

Immunohistochemistry

Human heart tissue from TTR amyloidosis patients were post-fixed in 4% formalin for 24 hours and embedded in paraffin. Hearts were cut to generate 8-16 µm thick sections. A series of sections was stained for either CGX304 or congo red (abcam, ab150663—manufacturer protocol). Tissue was washed for 5 minutes×3 times in xylene followed by ×2 in 100% ethanol. Than tissue was incubated in 0.3% $H_2O_2$ (in methanol) for 15 minutes in the dark, rinsed in DDW for 1 minute, followed by antigen retrieval (citrate buffer pH 6×1 in pressure chamber—120° C. for 30 minutes followed by 20 minutes of cooling), followed by CGX304 (1:1000) antibody incubation for 1 hour at room temperature. Then, sections were incubated in secondary antisera against mouse IgG (DAKO Envision FLEX SM802, manufacturer dilution). Antibody labeling was visualized by exposure to 0.5 mg/ml 3,3' diaminobenzidine (DAB—Zymotec), 2.5 mg/ml nickel ammonium sulfate, and 0.03% $H_2O_2$ in Tris buffer followed by hematoxylin (Mayer's—abcam—ab220365) counter stain. Sections were mounted on subbed slides, dehydrated to xylene and coverslipped with xylene base mounting buffer.

Generation of Short Term Rat Model of wtATTR and In Vivo Testing of CGX304

20 male (4 groups) Sprague-Dawley rats (200 grams) were anesthetized by Isoflurane before their chests were opened for aggregated TTR injection to the heart. Matrigel was added to aggregated TTR (30 µg in PBS; 50 µl volume) in a 1:1 volume ratio and loaded (100 µl) to a 1 ml syringe using a 27G needle and kept on ice until the rat was ready for injection. Control animals received sterile PBS and Matrigel (1:1) with no TTR. A single needle insertion into the apex of the rat's heart was used to spread the aggregated TTR for Technetium pyrophosphate ($^{99m}$Tc-PYP) scintigraphy detection assay model. Four mCi of $^{99m}$Tc-PYP were administered intravenously (IV) immediately after surgery. 30 minutes before surgery, animals received (IP) CGX304 (5 or 10 mg/kg) or non-relevant antibody 1G4-2 (sham) treatment. One hour later, animals underwent serial $^{99m}$Tc-PYP planar cardiac imaging and SPECT/CT scanning for TTR detection. Cardiac retention was assessed quantitatively using a volume of interest (VOI) over the left ventricle. Background was assessed using a posterior chest wall VOI. For biochemical studies, hearts were removed and tissues were immediately frozen and stored at −80° C. until used.

Immunohistochemistry of Aggregated TTR in Apex of Injected Rats

Rat hearts were post-fixed in 4% formalin for at least 4 hours and embedded in paraffin. Hearts were cut to generate 4 µm thick sections. A series of sections were stained with murine CGX304 or control isotype antibody. Tissue was washed for 5 minutes 3 times in xylene followed by 2 times in 100% ethanol. Then tissue was incubated in 0.3% $H_2O_2$ (in methanol) for 15 minutes in the dark, rinsed in DDW for 1 minute, followed by antigen retrieval (citrate buffer pH 6×1 in pressure chamber—120° C. for 30 minutes followed by 20 minutes of cooling), followed by murine CGX304 (1:1000) antibody incubation for 1 hour at room temperature. Then, sections were incubated in secondary antisera against mouse IgG (DAKO Envision FLEX SM802, manufacturer dilution). Antibody labeling was visualized by exposure to 0.5 mg/ml 3,3' diaminobenzidine (DAB—Zymotec), 2.5 mg/ml nickel ammonium sulfate, and 0.03% $H_2O_2$ in Tris buffer followed by hematoxylin (Mayer's—abcam—ab220365) counter stain. Sections were mounted on subbed slides, dehydrated to xylene, and coverslipped with xylene based mounting buffer.

Echocardiography in Rat Short Term Rat Model of wtATTR

Echocardiography was performed using a 12 MHz transducer (VIVID 6, GE medical) Conventional Left ventricular (LV) structure, and function was assessed from the parasternal, long (LAX) and short (SAX) axis views (at the level of the papillary muscles). Mitral inflow and aortic outflow were recorded by Doppler. Measurements were obtained off-line (EchoPAC BT13, General Electric). Chamber diameters, wall-thickness, and fractional shortening (FS) were measured by M-mode, in the SAX view, according to the "leading edge to leading edge" convention. Two-dimensional speckle-tracking strain analysis was performed offline. The LV was divided into 6 segments at the parasternal short axis view of the mid left ventricle as defined by the American Society of Echocardiography. Parameters including the peak systolic radial strain and radial strain rate (RS and RSr) and peak systolic circumferential strain and circumferential strain rate (SC and CSr) of each of the 6 segments were measured.

Immunohistochemistry of wtATTR Human Cardiac Biopsies

Human heart tissues from wtTTR amyloidosis patients were post-fixed in 4% formalin for 24 hours and embedded in paraffin. Hearts were cut to generate 8-16 µm thick sections. A series of sections was stained with either mouse CGX304, control mouse IgG, or Congo red (abcam, ab150663—manufacturer protocol). Tissue was washed for 5 minutes 3 times in xylene followed by 2 times in 100% ethanol. Then, tissue was incubated in 0.3% hydrogen peroxide ($H_2O_2$) (in methanol) for 15 minutes in the dark, rinsed in DDW for 1 minute, followed by antigen retrieval (citrate buffer pH 6 1 time in pressure chamber—120° C. for 30 minutes followed by 20 minutes of cooling), followed by CGX304/control IgG (1:1000) antibody incubation for 1 hour at room temperature. Then, sections were incubated in secondary antisera against mouse IgG (DAKO Envision FLEX SM802, manufacturer dilution). Antibody labeling was visualized by exposure to 0.5 mg/ml 3,3' diaminobenzidine (DAB—Zymotec), 2.5 mg/ml nickel ammonium sulfate, and 0.03% $H_2O_2$ in Tris buffer followed by hematoxylin (Mayer's—abeam—ab220365) counter stain. Sections were mounted on subbed slides, dehydrated to xylene, and coverslipped with xylene based mounting buffer.

Generation of an ELISA to Test the Presence of Circulating Aggregated TTR Employing CGX304 Derivatives Aiming to validate the ability of CGX304 to detect circulating levels of aggregated TTR, a capture ELISA was established. The details of the patients with wtATTR cardiac amyloidosis and control heart failure (HF) patients are provided in Table 3.

TABLE 3

Clinical characteristics of patients with wtATTR versus HF patients

|  | wtATTR (n = 27) | HF controls (n = 26) | P |
|---|---|---|---|
| Age; years [+/−SD] | 70.2 [+/−10.6] | 67.4 [+/−12.8] | 0.382 |
| Male Sex; % [n] | 51.9 [14] | 69.2 [18] | 0.264 |
| NYHA I-II; % [n] | 37.0 [10] | 69.2 [18] | 0.028 |
| NYHA III-IV; % [n] | 63.0 [17] | 30.8 [8] | 0.028 |
| Hypertension; % [n] | 81.5 [22] | 88.5 [23] | 0.704 |
| Diabetes: % [n] | 48.1 [13] | 34.6 [9] | 0.406 |
| Obesity; % [n] | 48.1 [13] | 34.6 [9] | 0.406 |
| Obstructive coronary artery disease; % [n] | 33.3 [9] | 26.9 [7] | 0.766 |
| Atrial fibrillation; % [n] | 44.4 [12] | 53.8 [14] | 0.587 |
| Pacemaker/CRT/ICD; % [n] | 66.7 [18] | 34.6 [9] | 0.029 |
| Pacemaker; % [n] | 29.6 [8] | 0 [0] | 0.004 |
| GFR with eGFR <60; % [n] | 40.7 [11] | 30.8 [8] | 0.569 |
| ACEi/ARB/ARNI; % [n] | 88.9 [24] | 96.2 [25] | 0.610 |
| Beta blockers; % [n] | 88.9 [24] | 96.2 [25] | 0.610 |
| MRA; % [n] | 44.4 [12] | 46.2 [12] | 1.000 |
| Diuretics; % [n] | 77.8 [21] | 61.5 [16] | 0.241 |
| LVEF; % [+/−SD] | 38.7 [+/−10.7] | 40.4 [+/−13.1] | 0.620 |

ELISA plates were coated with 100 μl/well of 4 μg/ml NeutrAvidin (ThermoFisher Scientific—cat #31000) and incubated overnight at 4° C. Wells were aspirated and washed 3 times (300 μl/well) with washing buffer (0.1% Tris Buffered Saline with 0.1% Tween 20 (TB ST)) followed by 1 hour incubation at room temperature with 300 μl/well blocking buffer (5% BSA/TB ST). Plates were then washed 3 times and incubated for 1.5 hours at room temperature with 100 μl/well biotinylated mouse CGX304 (2 μg/ml). Plates were washed three times, standard TTR and human serum samples were diluted in sample buffer (0.1% BSA/PBS), loaded into the plates (100 μl/well), and incubated for an additional 1.5 hours at room temperature. After additional washing steps, HRP-labeled mouse CGX304 was added to the wells (100 μl/well) and incubated for 1 hour at room temperature. Development was performed with substrate reagent containing tetramethylbenzidine and hydrogen peroxide (R&D systems, cat #DY999). The TTR concentration in samples was calculated from a standard curve ranging from 3.9 to 2000 ng/ml. The experiment was validated three times with triplicate sample repetition.

Statistical Analysis

Values shown in the Figures are presented as mean+/−SEM. P values for determination of the statistical significance of differences were calculated by means of paired, two-tailed Student's t test, one-way ANOVA with a post hoc Dunnet's or one-way ANOVA with Tukey's post test. The reproducibility of RS and CR measurements was analyzed with repeated measurements, in a blinded fashion, by an observer at two different time points in 5 randomly selected studies. Intra-observer agreement was evaluated by Bland-Altman analysis. In order to decrease non-constant variability, logarithmic transformation was performed. Intra-class Correlation Coefficient was calculated.

Example 1: Generation of Monoclonal Antibodies

Several clones of monoclonal antibodies (mAbs) were produced according to standard protocols by Balb/C mice immunization with 50 μg of variant mixtures of transthyretin (TTR) (Alexotech, Sweden) followed by three additional boosts. After confirming the presence of polyclonal anti-TTR antibodies (Abs) in the sera, mice were sacrificed. Cells were isolated from their spleens and hybridized with an SP2/0 myeloma line, followed by clonal screening for binding to TTR. The hybridomas were then grown in serum-free media for 2-3 weeks, and media were collected and concentrated by 30 kDa centricons (Biological Industries, Israel). Cross-reactivity of mAbs with human TTR was confirmed by ELISA.

Figure 1A:
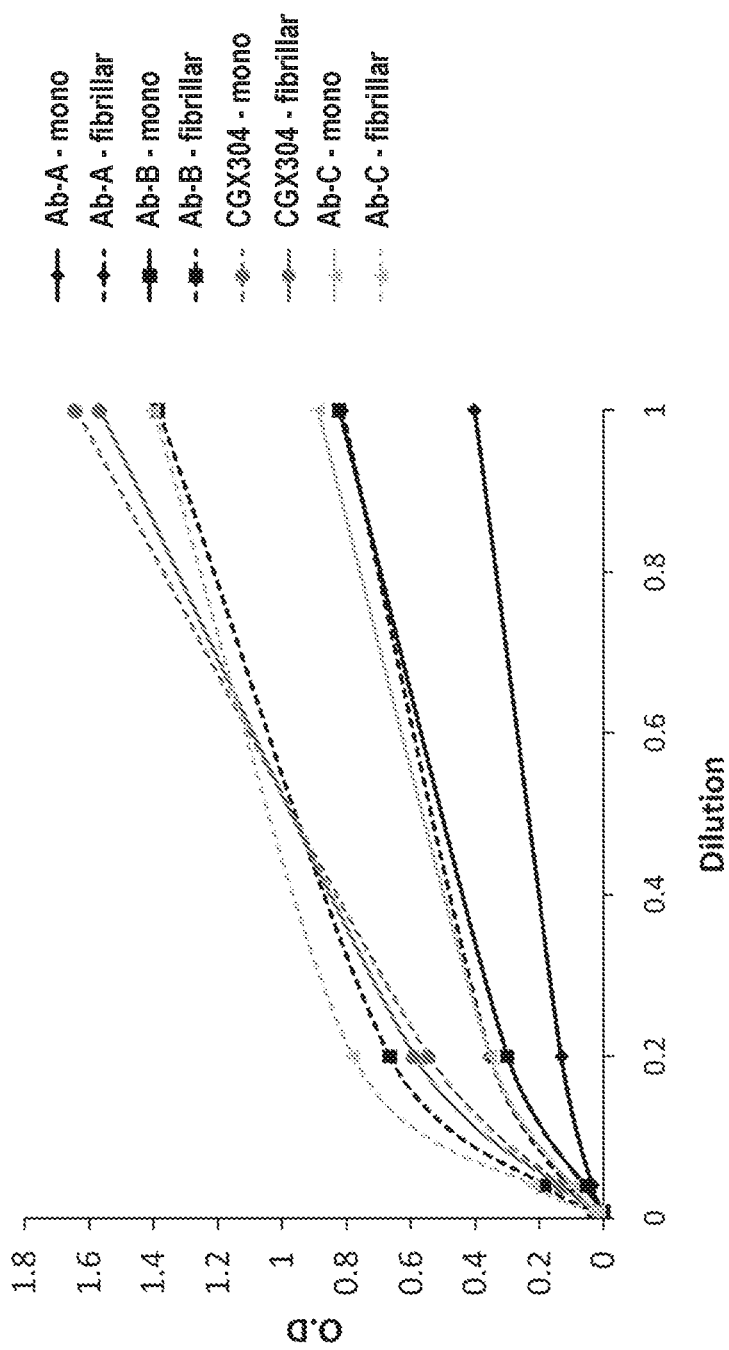
FIG. 1A is a graph showing binding of the mouse IgG antibodies Ab-A, Ab-B, CGX304, and Ab-C to transthyretin (TTR) in monomer and fibrillar forms. (See Example 1.)
Figure 1B:
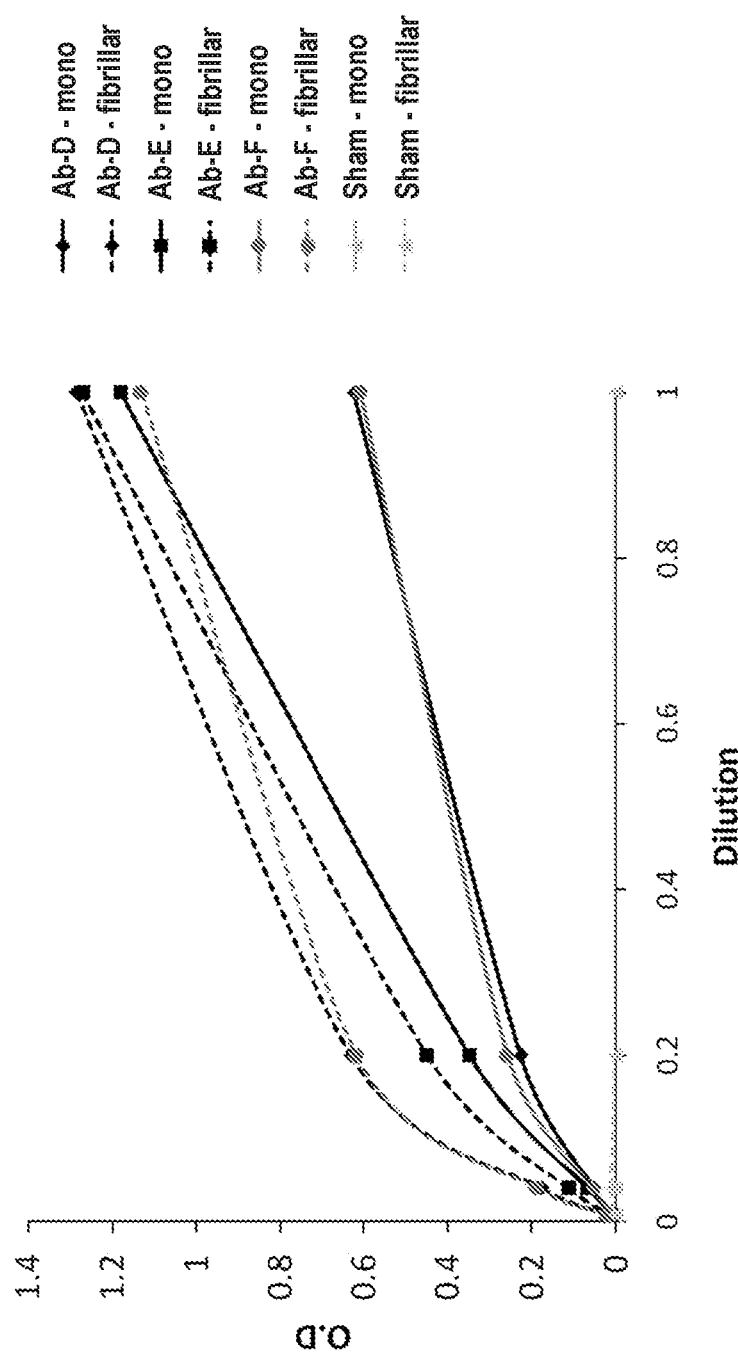
FIG. 1B is a graph showing binding of the mouse IgG antibodies Ab-D, Ab-E, and Ab-F and a sham antibody to TTR in monomer and fibrillar forms. (See Example 1.)

A standard ELISA was performed using variant mixtures of human TTR as the coating protein. As shown in FIGS. 1A and 1B, clones Ab-B, CGX304, Ab-C, Ab-D, Ab-E and Ab-F bound to the coating protein in a concentration-dependent manner. Clone Ab-A showed lower affinity binding under these assay conditions. Sham did not show binding at all (FIG. 1B).

Example 2: High Affinity Binding of Unique Clones

Figure 2:
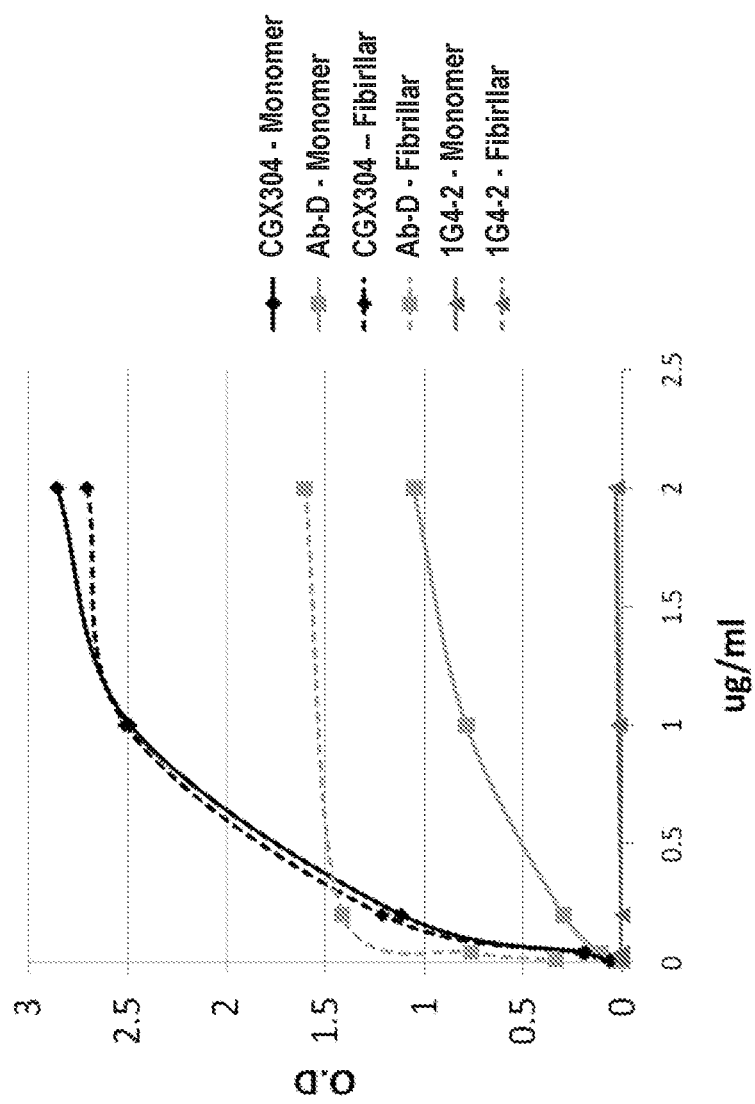
FIG. 2 is a graph showing the binding of CGX304, Ab-D, and shame (1G4-2) antibodies to monomer and fibrillar TTR by ELISA (See Example 2.)

Two selected unique clones (CGX304 and Ab-D) were chosen from a panel of a mixture of wild-type and mutated TTR-binding mouse IgG by their high affinity binding to monomer and fibrillar TTR seen in ELISA assay (FIG. 2). 1G4-2 was used as mouse IgG sham control. CGX304 clone was selected and tested for its high affinity to TTR fibril and monomer forms in surface Plasmon resonance (Biacore SPR system, GE Healthcare Life Sciences) (FIG. 3).

Figure 4:
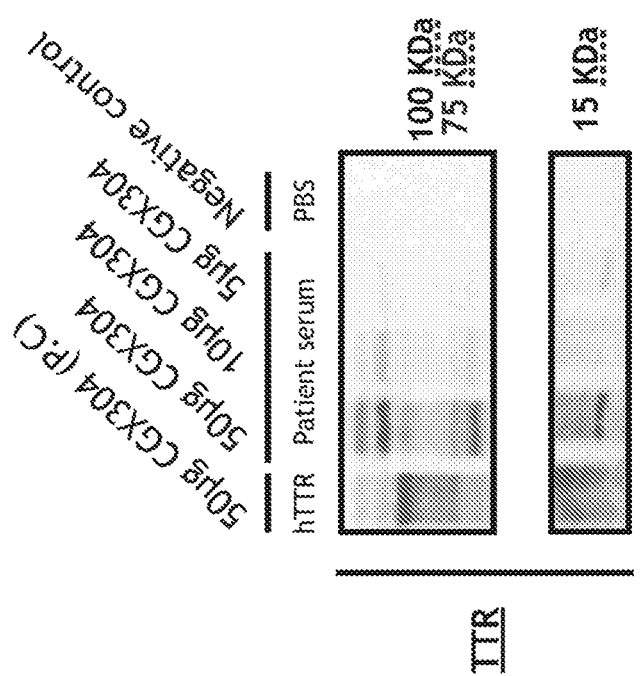
FIG. 4 shows immunoprecipitation of recombinant human TTR ("hTTR") or TTR from TTR-amyloidosis patient sera using CGX304 or a negative control. The TTR staining was performed using mouse monoclonal anti-human TTR antibody. (See Example 3.)

Example 3: CGX304 Immunoprecipitates Transthyretin from TTR Amyloidosis Patients' Sera Human serum derived from transthyretin amyloidosis patients were immunoprecipitated with CGX304 to determine the antibody's ability to bind endogenous human transthyretin. Three different amounts of CGX304 (50 μg, 10 μg, and 5 μg) were able to immunoprecipitate TTR from transthyretin amyloidosis patients' sera (FIG. 4). Samples were stained with a commercial polyclonal rabbit anti-human TTR antibody (GTX33557, GeneTex) (FIG. 4). Human recombinant TTR immunoprecipitation with 50 μg CGX304 was performed as positive control.

Example 4: CGX304 Avidly Binds Heart Tissues from Patients with TTR Amyloidosis

Figure 5:
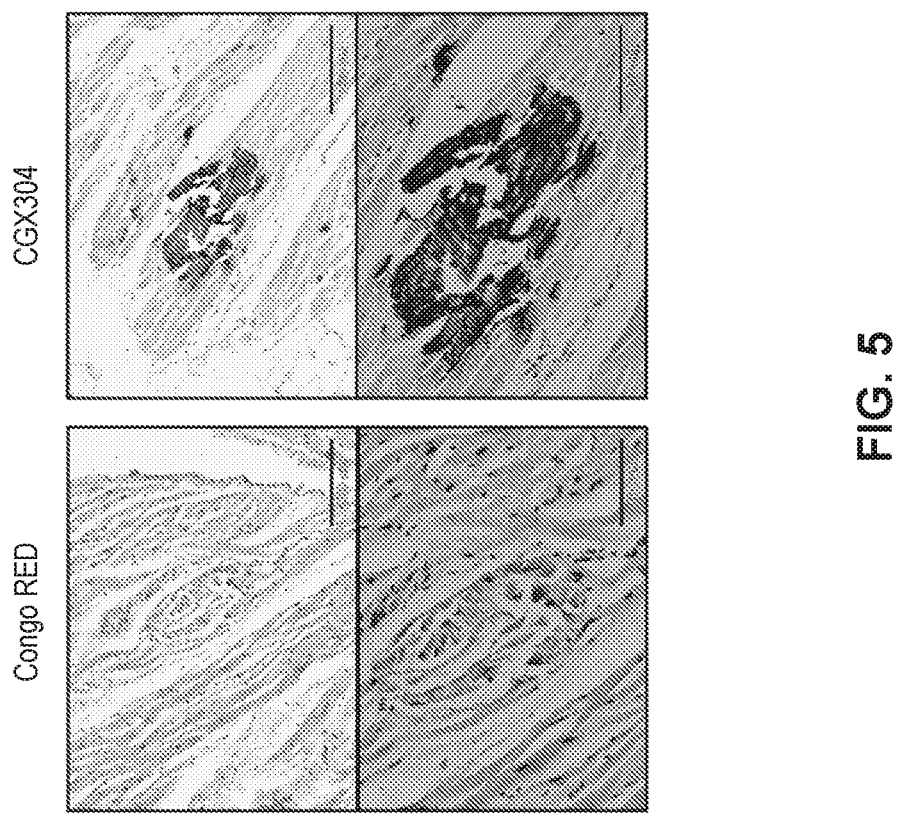
FIG. 5 shows immunohistochemical staining of a human heart tissue sample obtained from a TTR-amyloidosis patient using CGX304 (right panels) and congo red staining of the same human heart tissue sample (left panels). (See Example 4.)

CGX304 was able to bind avidly to its target transthyretin in a number of human heart transthyretin amyloidosis tissue samples seen by immunohistochemistry staining (FIG. 5), demonstrating its ability to recognize modified forms of TTR in multiple patients with TTR amyloidosis.

Figure 6:
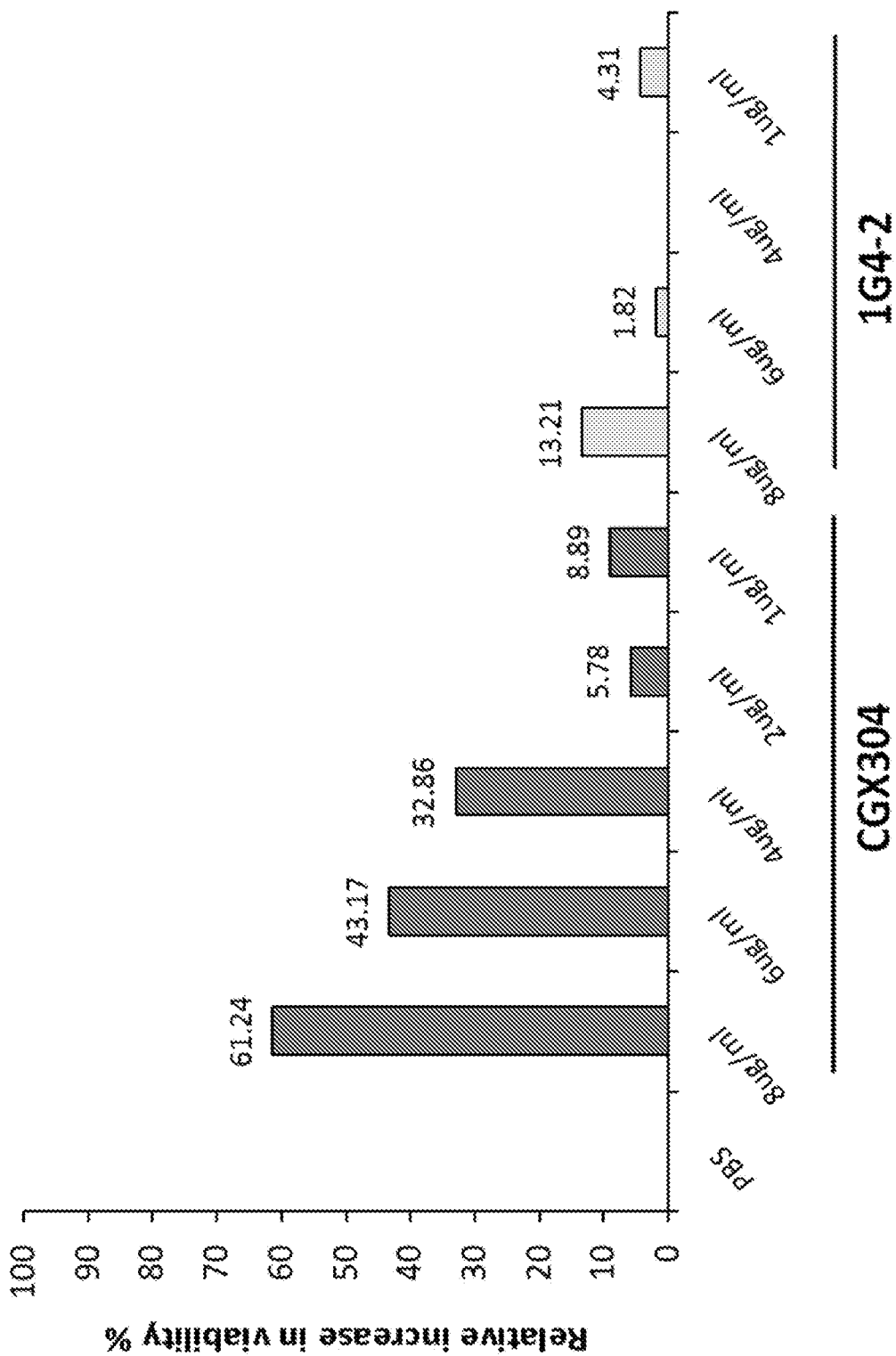
FIG. 6 is a bar graph showing the effect of CGX304 and a control antibody (1G4-2) on the viability of cardiomyocytes (H9c2 cell line) exposed to 2.5 µM fibrillar TTR. The y-axis represents the relative increase in cell viability resulting from treating with CGX304 or the control antibody (1G4-2) as compared to treatment with PBS. (See Example 5.)

Example 5: CGX304 Protects Rat Cardiomyocytes Cells from Fibrillar TTR Induced Toxicity The cytotoxicity of TTR fibrils was assessed on differentiated rat cardiomyocytes H9c2 cells using the 3-(4,5-dimethylthiazol-2-yl)-2,5-diphenyltetrazolium bromide (MTT) assay (FIG. 6). Fibrillar TTR had a toxic effect on cells in low concentrations as seen by the cell viability assay (FIG. 6). Incubation of fibrillar TTR in the presence of increasing concentrations of CGX304, showed an increase in cell viability in a dose-dependent manner, while no affect was seen in the presence of sham (1G4-2) (FIG. 6). Incubation of TTR fibrils in the presence of increasing concentrations of CGX304 showed a high increase in cell viability at concentrations of 8 µg/ml (~61%), 6 µg/ml (~43%), and 4 µg/ml (~33%) CGX304. CGX304 concentrations of 2 µg/ml and 1 µg/ml almost had no effect on cell viability (FIG. 6).

Figure 7A:
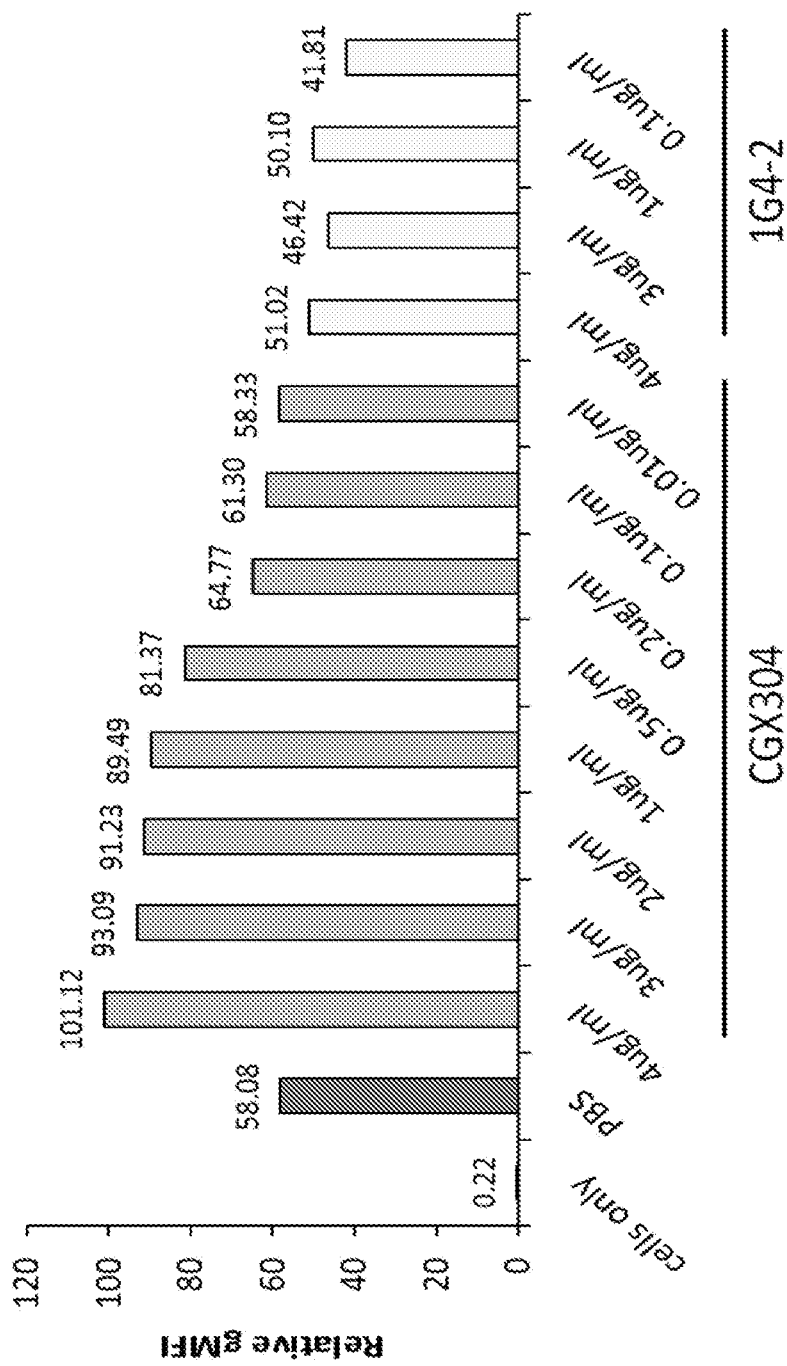
FIG. 7A is a bar graph showing the uptake of fluorescent fibrillar TTR by mouse microglia BV2 cells. The y-axis represents the relative geometric mean (gMFI) measured by flow cytometry. (See Example 6.)
Figure 7B:
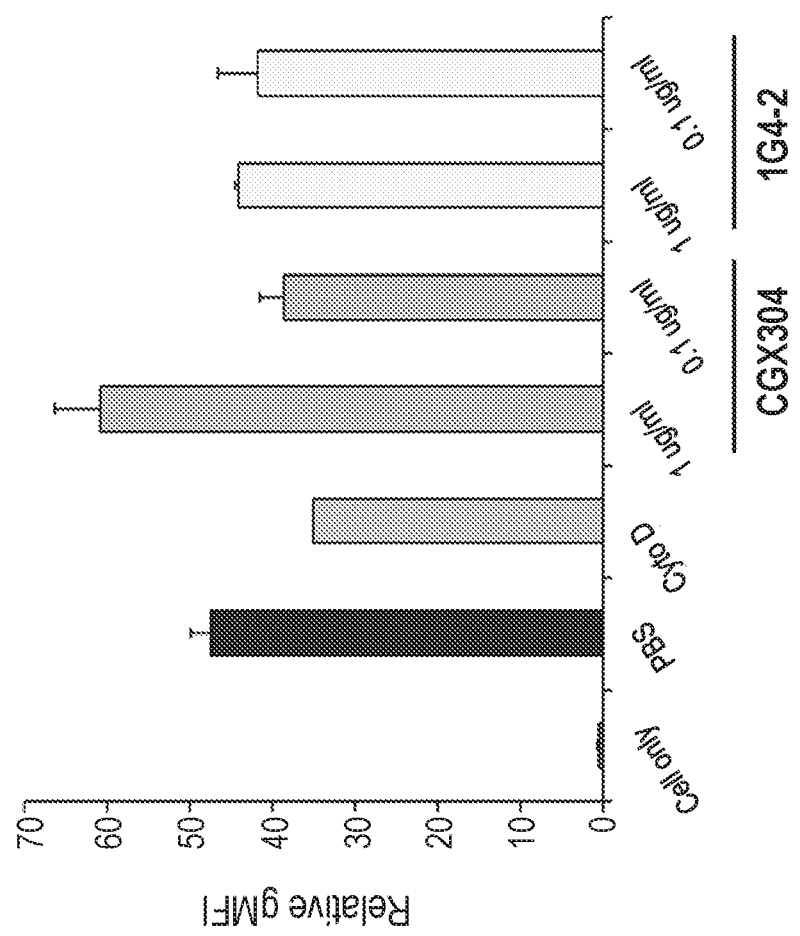
FIG. 7B is a bar graph showing the uptake of fluorescent fibrillar TTR by human monocytic THP-1 cells. The y-axis represents the relative geometric mean (gMFI) measured by flow cytometry. (See Example 6.)
Figure 7C:
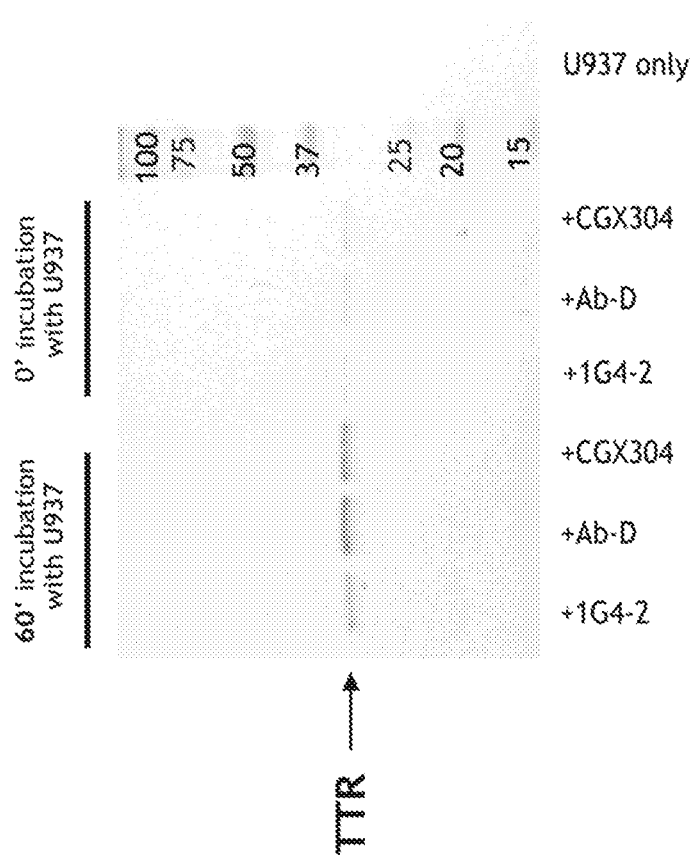
FIG. 7C shows the uptake of fibrillar TTR by human monocytes (U937) as measured by western blot. (See Example 6.)
Figure 7D:
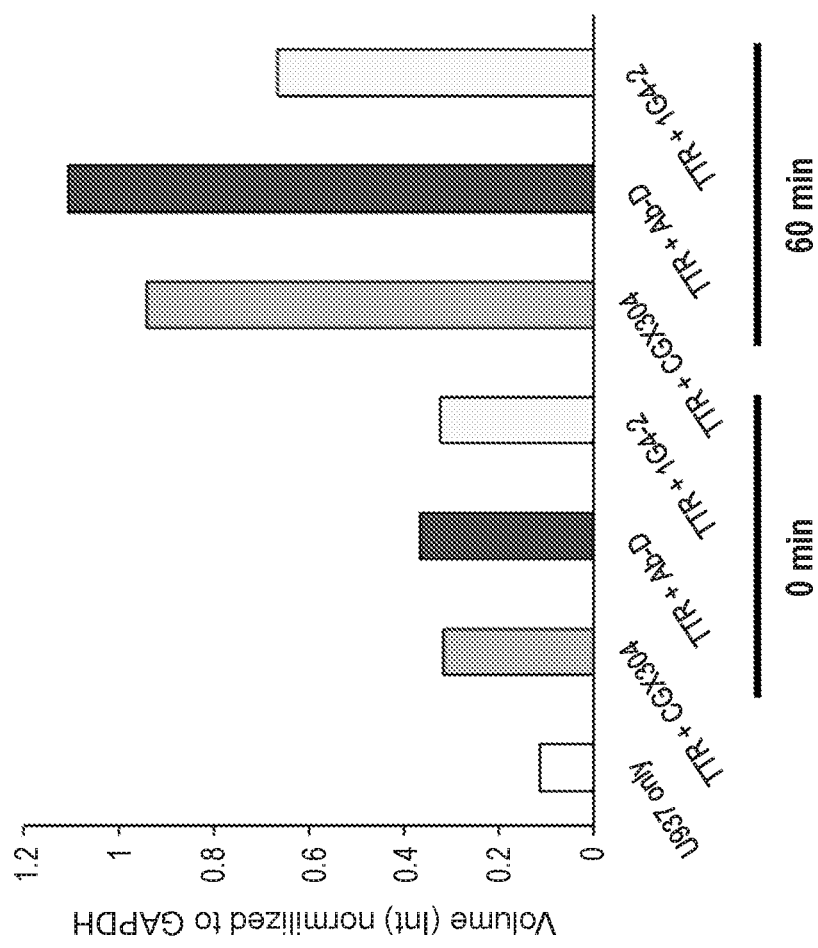
FIG. 7D is a bar graph showing the uptake of fibrillar TTR by human monocytes (U937) by western blot. The y-axis represents the volume intensity (pixels) normalized to GAPDH analyzed using image Lab software (Bio-rad). (See Example 6.)

Example 6: CGX304 Increases Uptake of TTR Fibrils in Human Monocytes and Mouse Microglia One of the main functions of macrophages and microglia in the immune system is phagocytosis. Phagocytosis is a major mechanism used to remove pathogens and cell debris, and it helps macrophages and microglia serve as antigen presenting cells, which are essential for T-cell immune response triggering. Flow cytometry was used to measure TTR fibrils conjugated to Alexafluor 488 cellular uptake (calculated by relative geomean fluorescent intensity (gMFI)) (FIGS. 7A, 7B, 7C, and 7D). Flow cytometry analysis shows that CGX304 increases mouse and human macrophages cellular uptake of fibrillar TTR conjugated to Alexafluor 488 (CGX304—relative gMFI~101) in a dose dependent manner compared to cells with no treatment (PBS—relative gMFI~58) and sham (1G4-2—relative gMFI~51) as seen in FIGS. 7A and 7B. FIGS. 7C and 7D show that both CGX304 (FIG. 7D—volume intensity~0.9) and Ab-D (FIG. 7D—volume intensity~1) increase human monocytes (U937) cellular uptake of fibrillar TTR after 60 minutes of incubation (FIGS. 7C and 7D) compared to sham (1G4-2) (FIG. 7D—volume intensity~0.6). No significant difference was seen after zero (0) minutes (cell lysate is prepared immediately after addition of CGX304/Ab-D/1G4-2—TTR complex) of incubation with cells (FIGS. 7C and 7D).

Example 7: CGX304 Clears Aggregated TTR Detected by PYP Scans Combined with Computer CT in Rodent Hearts Technetium pyrophosphate (99mTc-PYP) imaging has been used to diagnose transthyretin cardiac amyloidosis (ATTR-CA). 99mTc-PYP is FDA approved (for bone imaging as an adjunct in the diagnosis of acute myocardial infarction or as blood pool imaging agent), is readily available, and has been the preferred radiopharmaceutical for assessment of cardiac amyloidosis. The mechanism of myocardial transthyretin amyloid uptake of 99mTc-PYP is unclear, but it has been suggested that calcium in amyloid deposits binds to phosphate in these radiotracers.

Here, a new rat model was used to detect cardiac deposition of the wild-type, aggregated, misfolded TTR protein using 99mTc-PYP imaging (FIGS. 8A, 8B, and 8C). The advantage of this method is the ability to test and monitor the effects of new drugs on aggregated TTR clearance in a short period of time. FIG. 8C shows that CGX304 was detectable in the rat heart after treatment. PET-CT images show TTR clearance in the heart of CGX304 treated animals compare to sham (FIG. 8A; white arrows). FIG. 8B shows elevated levels of fluorescence intensity (F.I.) in sham+TTR treatment group (~2.3) compared to CGX304+TTR treatment group of animals (~1.5). There was no significant difference between the animal group with CGX304 treatment (CGX304+TTR) compared to the control group that received sham treatment and no TTR (sham-TTR; ~1.3). This result demonstrates the CGX304 clearance effect on aggregated TTR in the heart of rats.

Kidney impairment and proteinuria are also clinical features of ATTR. Nephropathy affects patients with late-onset neuropathy, low penetrance in the family, and cardiac dysrhythmias. Amyloid renal deposits commonly occur, even in the absence of urinary abnormalities. Therefore, technetium pyrophosphate (99mTc-PYP) imaging was also used for detection of kidney deposition of the wild-type aggregated misfolded TTR protein (FIGS. 9A, 9B, and 9C). The advantage of this method is the in vivo comparison between two identical organs, e.g., the ability to test the effects of a drug by comparison of the two sides (treated and untreated). PET-CT images show TTR clearance in the CGX304-treated left kidney compared to the sham-treated right kidney (FIG. 9A; white arrows). FIG. 9B shows elevated levels of fluorescence intensity (F.I.) in the right kidney as compared to the left kidney (right/left kidney>1) in all animals, indicating there was higher levels of TTR in the right kidney (sham) compared to the left kidney (CGX304). The immunoblot image in FIG. 9C demonstrates the effect of CGX304 on TTR clearance. There were higher tracers of TTR protein in the right kidney (R) compare to the left (L) in all animals.

Example 8: CGX304 Pharmacokinetics and Pharmacodynamics

FIG. 10A shows the PK values (mouse IgG1 concentration (ng/ml)) in rat serum 1 hour, 24 hours, 72 hours, 7 days, and 28 days post intravenous (IV) injection. Each group received a different initial concentration of CGX304 (0.5 mg/kg, 2.5 mg/kg, and 10 mg/kg) IV. CGX304 half-life value is ~187.5 hours (FIG. 10A). FIG. 10B shows free endogenous rat pre-albumin (TTR) levels (PD values) in blood serum of same group of animals. FIG. 10C shows levels of CGX304 in rat hearts 28 days after IV administration at various doses.

Example 9: CGX304 Stains Aggregated TTR in Cardiac Samples from Patients with wtATTR To test the ability of mouse CGX304 to detect aggregated TTR in patients, tissue samples from hearts of human WT ATTR cardiac amyloidosis patients were immunostained with mouse CGX304 or control IgG and compared to Congo red staining. CGX304 was able to bind avidly to its target transthyretin in a number of human heart transthyretin amyloidosis tissue samples as seen by immunohistochemistry staining (FIG. 12). These results demonstrate the ability of CGX304 to recognize modified forms of TTR in multiple patients with significantly higher sensitivity than congo red staining. There was no staining of modified forms seen using the mouse control IgG antibody.

Example 10: CGX304 Clears Aggregated TTR Evident by In Vivo PYP Scintigraphy Signals A short term rat model of wtATTR was used to assess the ability of CGX304 to clear aggregated TTR. Aggregated TTR was injected into the hearts of rats that received either CGX304 or a control (sham) antibody, and PYP was used to detect aggregated TTR (as described in the materials and methods).

The results are shown in FIG. 13. Detectable levels of aggregated TTR were seen in the rat heart after treatment. FIG. 13 shows a decrease in PYP cardiac uptake (% Normalized TTR uptake ratio) in 10 mg/kg (p=0.0079) and 5 mg/kg (p=0.042) CGX304+TTR treatment groups (70.87% and 73.95%, respectively) relative to the sham+TTR treatment group (100%). There was not a significant difference between the group treated with 1 mg/kg CGX304

(CGX304+TTR) compared to the control group that received sham treatment and TTR (sham+TTR; 94.39%). This result demonstrates that CGX304 clears and degrades the aggregated TTR in rat hearts.

Example 11: CGX304 Stains Aggregated TTR in Apex Injected Rats

The ability of CGX304 to detect aggregated TTR was also observed in rats with aggregated TTR injected into the heart apex. CGX304 was able to bind avidly to aggregated TTR injected into the apex of rats hearts as seen by immunohistochemistry staining (FIG. 11). These results demonstrate the ability of CGX304 to recognize the injected modified TTR in the PYP rat model. There was no staining of TTR seen in control rats (rats injected with sham (-TTR)).

Example 12: Functional Improvement in Cardiac Performance by CGX304 in the Experimental ATTR Model Echocardiography was performed pre and post aggregated TTR injections (with/without IV treatment) in the short term rat model of wtATTR. Rats were injected with aggregated TTR injection to the hearts followed by CGX304 (5 mg/kg) or sham treatment. The resulting changes in left ventricular size and function are shown in Table 4.

There was no change in left ventricular dimension between the groups. There was also no change in the conventional systolic function parameters, e.g., fractional shortening. However, in 5 control rats there was a significant decrease in radial strain (FIGS. 14A and 14D) and in circumferential strain rate S (FIG. 14B) ($p=0.017$ and $p=0.007$, respectively). In the CGX304-treated group, these changes in the parameter of systolic deformation were blunted and not statistically significant. There were no significant changes in diastolic function, including the ratios ME/MA and E/E'. The circumferential strain rate E increased, and the A decreased not significantly in both groups. The ratio of circumferential strain rate E to A changed less in the treatment group (FIG. 14C). The functional changes seen in deformation analysis are usually more sensitive and appear earlier than the change in LVEF and this was shown in various experimental and clinical studies (Popovic et al., *AM J. Physiol Heart Circ Physiol* 292(6): H2809-16 (2007); Pagourelias et al., *Circ Cardiovasc Imaging* 10(3):e005588 (2017)). The reproducibility of RS and CS measurements are shown in FIG. 14E. The assessment of RS and CS parameters shows a good intra-observer agreement with low mean bias (0.018±0.208, 95% limits of agreement of −0.3892-0.426) and good reproducibility, with an intra-class correlation coefficients of 0.974 (95% CI 0.932-0.990).

TABLE 4

Echocardiographic characteristics of rats before and after TTR injection with and without CGX304

| | | Sham (n = 5) | | | CGX304 (n = 4) | | |
|---|---|---|---|---|---|---|---|
| | | Mean | Std. Deviation | P value | Mean | Std. Deviation | P value |
| RS (%) | Baseline | 33.20 | 7.46 | 0.02 | 30.25 | 5.32 | 0.051 |
| | post | 23.40 | 4.51 | | 27.00 | 6.27 | |
| RSr-S (s − 1) | Baseline | 6.20 | 2.39 | 0.90 | 8.39 | 2.87 | 0.740 |
| | post | 6.00 | 1.87 | | 7.75 | 1.26 | |
| RSr-E (s − 1) | Baseline | −7.50 | 3.91 | 0.27 | −6.00 | 2.16 | 0.916 |
| | post | −5.20 | 0.84 | | −6.25 | 2.99 | |
| RSr-A (s − 1) | Baseline | −5.36 | 1.32 | 0.20 | −4.67 | 3.06 | 1.000 |
| | post | −2.16 | 4.07 | | −4.67 | 0.58 | |
| CS (%) | Baseline | −10.80 | 2.77 | 0.42 | −10.75 | 2.99 | 0.448 |
| | post | −11.98 | 1.45 | | −12.00 | 2.16 | |
| CSr-s (s − 1) | Baseline | −5.00 | 0.71 | 0.01 | −4.13 | 0.63 | 0.080 |
| | post | −3.86 | 0.77 | | −4.75 | 0.96 | |
| CSr-E (s − 1) | Baseline | 3.20 | 0.45 | 0.20 | 3.58 | 0.72 | 0.336 |
| | post | 4.06 | 0.90 | | 4.50 | 1.29 | |
| CSr-A (s − 1) | Baseline | 3.60 | 1.14 | 0.07 | 2.75 | 0.50 | 0.06 |
| | post | 3.00 | 1.00 | | 3.50 | 0.58 | |
| CSr-E/CSr-A | Baseline | 0.98 | 0.40 | 0.006 | 1.29 | 0.40 | 0.78 |
| | post | 1.42 | 0.30 | | 1.27 | 0.20 | |
| DD (mm) | Baseline | 0.66 | 0.09 | 0.62 | 0.65 | 0.10 | 0.18 |
| | post | 0.68 | 0.08 | | 0.70 | 0.08 | |
| SD (mm) | Baseline | 0.40 | 0.07 | 0.62 | 0.35 | 0.06 | 0.39 |
| | post | 0.42 | 0.04 | | 13.83 | 26.78 | |
| FS (%) | Baseline | 38.00 | 4.95 | 0.68 | 45.75 | 5.56 | 0.14 |
| | post | 36.60 | 2.30 | | 38.00 | 3.16 | |
| ME/MA | Baseline | 1.76 | 1.05 | 0.55 | 1.31 | 0.25 | 0.89 |
| | post | 1.36 | 0.59 | | 1.27 | 0.45 | |
| E/E' | Baseline | 0.23 | 0.07 | 0.38 | 0.15 | 0.01 | 0.67 |
| | post | 0.15 | 0.05 | | 0.15 | 0.01 | |
| TDI-IE (cm · s) | Baseline | 3.33 | 0.58 | 0.53 | 4.50 | 0.71 | 0.67 |
| | post | 4.00 | 1.00 | | 3.50 | 0.71 | |

RS = Radial strain, RSr = Radial strain rate, CS = Circumferential strain, CSr = Circumferential strain rate, DD diastolic diameter, SD = systolic diameter, FS = fractional shortening, ME-mitral E wave, MA = mitral A wave, TDI tissue Doppler imaging. All the P values are comparison of baseline and post injection image.

Example 13: An ELISA Employing CGX304 Detects High Levels of Shed Aggregated TTR in the Sera of Patients with wtATTR Cardiac Amyloidosis An ELISA assay employing Ab-A detected the presence of circulating aggregated TTR in sera of patients with wtATTR cardiac amyloidosis (FIG. 15, wtATTR) compared to control heart failure patients (FIG. 15, Control). The assay was conducted on 43 patients with wtATTR cardiac amyloidosis and 42 control patients with heart failure matched by their baseline clinical characteristics. The diagnosis of wtATTR cardiac amyloidosis was based on PYP scintigraphy after ruling out light chain cardiac amyloidosis.

What is claimed is:

1. An antibody or antigen-binding fragment thereof capable of binding human transthyretin (TTR), wherein the antibody or antigen-binding fragment thereof comprises a complementary determining region (CDR) H1 comprising the amino acid sequence of SEQ ID NO:1 (GYTFTSYY), a CDR H2 comprising the amino acid sequence of SEQ ID NO:2 (IYPGNVNT), a CDR H3 comprising the amino acid sequence of SEQ ID NO:3 (ARTYFDY), a CDR L1 comprising the amino acid sequence of SEQ ID NO:4 (SSVSY), a CDR L2 comprising the amino acid sequence of SEQ ID NO:5 (DTS), and a CDR3 L3 comprising the amino acid sequence of SEQ ID NO:6 (QQWSSKSFT).

2. The antibody or antigen-binding fragment thereof of claim 1 wherein the antibody or antigen-binding fragment thereof binds to human TTR monomers and/or human TTR fibrils.

3. The antibody or antigen-binding fragment of claim 1, wherein the antibody or antigen-binding fragment is an antigen-binding fragment, wherein the antigen-binding fragment comprises a Fab, Fab', F(ab')$_2$, single chain Fv(scFv), disulfide linked Fv, intrabody, minibody, F(ab')$_3$, 2 tetrabody, triabody, diabody, single domain antibody, DVD-Ig, Fcab, mAb$^2$, (scFv)$_2$, or scFv-Fc.

4. An isolated polynucleotide comprising a first nucleic acid molecule encoding the heavy chain variable region or heavy chain of the antibody or antigen-binding fragment thereof of claim 1 and a second nucleic acid molecule encoding the light chain variable region or light chain of the antibody or antigen-binding fragment thereof of claim 1.

5. An isolated vector comprising the polynucleotide of claim 4.

6. A host cell comprising the polynucleotide of claim 4.

7. A method of producing an antibody or antigen-binding fragment thereof that binds to human TTR comprising culturing the host cell comprising the isolated polynucleotide of claim 4 so that the first nucleic acid molecule and the second nucleic acid molecule are expressed and the antibody or antigen-binding fragment thereof is produced.

8. An isolated antibody or antigen-binding fragment thereof that is produced by the method of claim 7.

9. A pharmaceutical composition comprising the antibody or antigen-binding fragment thereof of claim 1 and a pharmaceutically acceptable excipient.

10. A method for detecting TTR in a sample or precipitating TTR from a sample comprising contacting the sample with the antibody or antigen-binding fragment thereof of claim 1.

11. A method for increasing the uptake of TTR aggregates by an immune cell exposed to TTR aggregates comprising contacting the immune cell with the antibody or antigen-binding fragment of claim 1.

12. A method for decreasing the toxicity of TTR aggregates on a cell exposed to TTR aggregates comprising contacting the cell with the antibody or antigen-binding fragment thereof of claim 1.

13. A method of inhibiting the accumulation of TTR aggregates in an organ exposed to TTR aggregates comprising contacting the organ with the antibody or antigen-binding fragment thereof of claim 1.

14. A method of treating a TTR amyloidosis in a subject comprising administering to the subject the antibody or antigen-binding fragment thereof of claim 1.

15. A method for diagnosing a TTR amyloidosis in a subject comprising administering to the subject the antibody or antigen-binding fragment thereof of claim 1.

16. A kit comprising the antibody or antigen-binding fragment thereof of claim 1 and a) a detection reagent, b) TTR antigen, c) a notice that reflects approval for use or sale for human administration, or d) a combination thereof.

* * * * *

UNITED STATES PATENT AND TRADEMARK OFFICE
CERTIFICATE OF CORRECTION

| | | |
|---|---|---|
| PATENT NO. | : 12,006,357 B2 | |
| APPLICATION NO. | : 17/255796 | |
| DATED | : June 11, 2024 | |
| INVENTOR(S) | : Michael Fassler and Jacob George | |

It is certified that error appears in the above-identified patent and that said Letters Patent is hereby corrected as shown below:

In the Claims

In Column 53, Lines 56 and 57, Claim 3, please replace "2 tetrabody" with --tetrabody--.

Signed and Sealed this
Seventeenth Day of September, 2024

Katherine Kelly Vidal
Director of the United States Patent and Trademark Office

```
                              SEQUENCE LISTING

<160> NUMBER OF SEQ ID NOS: 12

<210> SEQ ID NO 1
<211> LENGTH: 8
<212> TYPE: PRT
<213> ORGANISM: Artificial Sequence
<220> FEATURE:
<223> OTHER INFORMATION: CGX304 CDR H1

<400> SEQUENCE: 1

Gly Tyr Thr Phe Thr Ser Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: CGX304 CDR H2

<400> SEQUENCE: 2

Ile Tyr Pro Gly Asn Val Asn Thr
1               5

<210> SEQ ID NO 3
<211> LENGTH: 7
<212> TYPE: PRT
<213> ORGANISM: Artificial Sequence
<220> FEATURE:
<223> OTHER INFORMATION: CGX304 CDR H3

<400> SEQUENCE: 3

Ala Arg Thr Tyr Phe Asp Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: CGX304 CDR L1

<400> SEQUENCE: 4

Ser Ser Val Ser Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: CGX304 CDR L2

<400> SEQUENCE: 5

Asp Thr Ser
1

<210> SEQ ID NO 6
```

```
<211> LENGTH: 9
<212> TYPE: PRT
<213> ORGANISM: Artificial Sequence
<220> FEATURE:
<223> OTHER INFORMATION: CGX304 CDR L3-Kabat

<400> SEQUENCE: 6

Gln Gln Trp Ser Ser Lys Ser Phe Thr
1               5

<210> SEQ ID NO 7
<211> LENGTH: 147
<212> TYPE: PRT
<213> ORGANISM: Homo sapiens

<400> SEQUENCE: 7

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
                20                  25                  30

Met Val Lys Val Leu Asp Ala Val Arg Gly Ser Pro Ala Ile Asn Val
                35                  40                  45

Ala Val His Val Phe Arg Lys Ala Ala Asp Asp Thr Trp Glu Pro Phe
50                      55                      60

Ala Ser Gly Lys Thr Ser Glu Ser Gly Glu Leu His Gly Leu Thr Thr
65                      70                      75                      80

Glu Glu Glu Phe Val Glu Gly Ile Tyr Lys Val Glu Ile Asp Thr Lys
                    85                  90                  95

Ser Tyr Trp Lys Ala Leu Gly Ile Ser Pro Phe His Glu His Ala Glu
                100                 105                 110

Val Val Phe Thr Ala Asn Asp Ser Gly Pro Arg Arg Tyr Thr Ile Ala
                115                 120                 125

Ala Leu Leu Ser Pro Tyr Ser Tyr Ser Thr Thr Ala Val Val Thr Asn
                130                 135                 140

Pro Lys Glu
145

<210> SEQ ID NO 8
<211> LENGTH: 5
<212> TYPE: PRT
<213> ORGANISM: Artificial Sequence
<220> FEATURE:
<223> OTHER INFORMATION: CGX304 CDR H1-Kabat

<400> SEQUENCE: 8

Ser Tyr Tyr Ile His
1               5

<210> SEQ ID NO 9
<211> LENGTH: 17
<212> TYPE: PRT
<213> ORGANISM: Artificial Sequence
<220> FEATURE:
<223> OTHER INFORMATION: CGX304 CDR H2-Kabat

<400> SEQUENCE: 9

Trp Ile Tyr Pro Gly Asn Val Asn Thr Lys Tyr Asn Glu Lys Phe Lys
1               5                   10                  15

Gly

<210> SEQ ID NO 10
```

```
<211> LENGTH: 5
<212> TYPE: PRT
<213> ORGANISM: Artificial Sequence
<220> FEATURE:
<223> OTHER INFORMATION: CGX304 CDR H3-Kabat

<400> SEQUENCE: 10

Thr Tyr Phe Asp Tyr
1               5

<210> SEQ ID NO 11
<211> LENGTH: 10
<212> TYPE: PRT
<213> ORGANISM: Artificial Sequence
<220> FEATURE:
<223> OTHER INFORMATION: CGX304 CDR L1-Kabat

<400> SEQUENCE: 11

Ser Ala Ser Ser Ser Val Ser Tyr Met His
1               5                   10

<210> SEQ ID NO 12
<211> LENGTH: 7
<212> TYPE: PRT
<213> ORGANISM: Artificial Sequence
<220> FEATURE:
<223> OTHER INFORMATION: CGX304 CDR L2-Kabat

<400> SEQUENCE: 12

Asp Thr Ser Lys Leu Ala Ser
1               5
```